(12) United States Patent
DeLuca et al.

(10) Patent No.: US 8,193,169 B2
(45) Date of Patent: Jun. 5, 2012

(54) (20R)-2α-METHYL-19,26,2-TRINOR-VITAMIN D ANALOGS

(75) Inventors: Hector F. DeLuca, Deerfield, WI (US);
Pawel Grzywacz, Madison, WI (US);
Lori A. Plum, Arena, WI (US);
Margaret Clagett-Dame, Deerfield, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 12/171,085

(22) Filed: Jul. 10, 2008

(65) Prior Publication Data
US 2008/0300223 A1    Dec. 4, 2008

Related U.S. Application Data

(63) Continuation-in-part of application No. 11/697,434, filed on Apr. 6, 2007.

(60) Provisional application No. 60/744,386, filed on Apr. 6, 2006.

(51) Int. Cl.
*A61K 31/59* (2006.01)
*C07C 401/00* (2006.01)
*C07C 35/17* (2006.01)
*A61P 17/00* (2006.01)

(52) U.S. Cl. .......... 514/167; 552/653

(58) Field of Classification Search ............ 552/653; 514/167, 653
See application file for complete search history.

(56) References Cited

U.S. PATENT DOCUMENTS

| | | | |
|---|---|---|---|
| 5,063,221 A | 11/1991 | Nishii et al. | |
| 5,086,191 A | 2/1992 | DeLuca et al. | |
| 5,536,713 A | 7/1996 | Deluca et al. | |
| 5,545,633 A | 8/1996 | Bretting | |
| 5,695,794 A * | 12/1997 | Stark et al. | 426/2 |
| 5,843,928 A | 12/1998 | DeLuca et al. | |
| 5,929,056 A | 7/1999 | Mourino et al. | |

(Continued)

FOREIGN PATENT DOCUMENTS

WO    98/41501    9/1998

(Continued)

OTHER PUBLICATIONS

Baggiolini et al., "Stereocontrolled Total Synthesis of 1α,25-Dihydroxycholecalciferol and 1α,25-Dihydroxyergocalciferol," Journal of Organic Chemistry, 51, pp. 3098-3108, (1986).

(Continued)

*Primary Examiner* — Sabiha Qazi
(74) *Attorney, Agent, or Firm* — Andrus, Sceales, Starke & Sawall, LLP

(57) ABSTRACT

This invention discloses (20R)-2α-methyl-19,26,27-trinor-vitamin D analogs, and specifically (20R)-2α-methyl-19,26,27-trinor-1α,25-dihydroxyvitamin $D_3$, and pharmaceutical uses therefor. This compound exhibits transcription activity as well as pronounced activity in arresting the proliferation of undifferentiated cells and inducing their differentiation to the monocyte thus evidencing use as an anti-cancer agent and for the treatment of skin diseases such as psoriasis as well as skin conditions such as wrinkles, slack skin, dry skin and insufficient sebum secretion. This compound also shows very low activity in vivo on bone calcium mobilization and intestinal calcium transport activity compared to the native hormone 1α,25-dihydroxyvitamin $D_3$, and therefore may be used to treat autoimmune disorders or inflammatory diseases in humans as well as renal osteodystrophy. This compound may also be used for the treatment or prevention of obesity.

79 Claims, 5 Drawing Sheets

HL-60 Cell Differentiation $EC_{50}$:  $1,25(OH)_2D_3 = 2 \times 10^{-9}$ M
B9 $= 3 \times 10^{-8}$ M

U.S. PATENT DOCUMENTS

| | | | |
|---|---|---|---|
| 5,945,410 | A | 8/1999 | DeLuca et al. |
| 6,248,374 | B1 * | 6/2001 | Murray et al. .................. 426/72 |
| 6,399,797 | B1 | 6/2002 | von Daehne et al. |
| 6,521,608 | B1 * | 2/2003 | Henner et al. ................. 514/167 |
| 6,566,352 | B1 | 5/2003 | DeLuca et al. |
| 6,579,861 | B2 | 6/2003 | DeLuca et al. |
| 6,627,622 | B2 | 9/2003 | DeLuca et al. |
| 7,241,909 | B2 * | 7/2007 | DeLuca et al. ................. 552/653 |
| 7,528,122 | B2 * | 5/2009 | DeLuca et al. ................. 514/167 |
| 7,803,789 | B2 * | 9/2010 | Deluca et al. ................. 514/167 |
| 2003/0158157 | A1 | 8/2003 | DeLuca et al. |
| 2007/0249567 | A1 | 10/2007 | DeLuca et al. |
| 2007/0254857 | A1 | 11/2007 | DeLuca et al. |
| 2007/0270391 | A1 | 11/2007 | DeLuca et al. |

FOREIGN PATENT DOCUMENTS

| | | |
|---|---|---|
| WO | 02/05823 | 1/2002 |
| WO | 2006/119309 | 11/2006 |

OTHER PUBLICATIONS

Collins et al, "Normal Functional Characteristics of Cultured Human Promyelocytic Leukemia Cells (HL-60) After Inducation of Differentiation by Dimethylsulfoxide," The Journal of Experimental Medicine, vol. 149, pp. 969-974, (1979).

Darwish et al, "Identification of Transcription Factor That Binds to the Promoter Region of the Human Parathyroid Hormone Gene," Archives of Biochemistry and Biophysics, vol. 365, No. 1, pp. 123-130, (1999).

Lythgoe et al, "Calciferol and its Relatives. Part22. A Direct Total Synthesis of Vitamin D2 and Vitamin D3," J. Chem. Soc. Perkin Trans. 1, p. 590, (1978).

Lythgoe, "Synthetic Approaches to Vitamin D and its Relatives," Chem. Soc. Rev. 9, p. 449, (1983).

Miyamoto et al, "Synthetic Studies of Vitamin D Analogues. XIV. Synthesis and Calcium Regulating Activity of Vitamin D3 Analogues Bearing a Hydroxyalkoxy Group at the 2β-Position," Chem. Pharm. Bull., vol. 41 No. 6, pp. 1111-1113, (1993).

Nishii et al, "The Development of Vitamin D3 Analogues for the Treatment of Osteoporosis," Osteoporosis Int., Suppl. 1, pp. S190-193, (1993).

Okano et al, "Regulatory Activities of 2β-(3-Hydroxypropoxy)-1α,25-Dihydroxy-Vitamin D3, a Novel Synthetic Vitamin D3 Derivative, on Calcium Metabolism," Biochemical and Biophysical Research Communications, vol. 163 No. 3, pp. 1444-1449, (1989).

Ostrem et al, "24- and 26-homo-1,25-dihydroxyvitamin D3: Preferential activity in inducing differentiation of human leukemia cells HL-60 in vitro," Proc. Natl. Acad. Sci. USA, vol. 84, pp. 2610-2614, (1987).

Perlman et al, "Novel Synthesis of 19-Nor-Vitamin D Compounds," Tetrahedron Letters, vol. 32 No. 52, pp. 7663-7666, (1991).

Perlman et al, "1α,25-Dihydroxy-19-Nor-Vitamin D3. A Novel Vitamin D-Related Compound with Potential Therapeutic Activity," Tetrahedron Letters, vol. 31 No. 13, pp. 1823-1824, (1990).

Posner et al, "Stereocontrolled Total Synthesis of Calcitriol Derivatives: 1,25-Dihydroxy-2-(4'-hydroxybutyl)vitamin D3 Analogs of an Osteoporosis Drug," Journal of Organic Chemistry, vol. 59 No. 25, pp. 7855-7861, (1994).

Posner et al, "2-Fluoroalkyl A-Ring Analogs of 1,25-Dihydroxyvitamin D3. Stereocontrolled Total Synthesis via Intramolecular and Intermolecular Diets—Alder Cycloadditions. Preliminary Biological Testing," Journal of Organic Chemistry, vol. 60 No. 14, pp. 4617-4628, (1995).

Sardina et al, "Studies on the Synthesis of Side-Chain Hydroxylated Metabolites of Vitamin D. 2. Stereocontrolled Synthesis of 25-Hydroxyvitamin D2," J. Org. Chem., 51, pp. 1264-1269, (1986).

Toh et al, "Studies on a Convergent Route to Side-Chain Analogues of Vitamin D: 25-Hydroxy-23-Oxavitamin D3," J. Org. Chem., 48, 1414, (1983).

International Search Report/Written Opinion; PCT/IB2007/003919; Issued Mar. 27, 2008.

* cited by examiner

(20R)-2α-METHYL-19,26,2-TRINOR-VITAMIN D ANALOGS

CROSS REFERENCE TO RELATED APPLICATIONS

The present patent application is a continuation-in-part of U.S. application Ser. No. 11/697,434 filed Apr. 6, 2007, which application claims priority to U.S. Provisional Patent Application No. 60/744,386 filed Apr. 6, 2006.

BACKGROUND OF THE INVENTION

This invention relates to vitamin D compounds, and more particularly to (20R)-2α-methyl-19,26,27-trinor-vitamin D analogs and their pharmaceutical uses.

The natural hormone, 1α,25-dihydroxyvitamin $D_3$ and its analog in ergosterol series, i.e. 1α,25-dihydroxyvitamin $D_2$ are known to be highly potent regulators of calcium homeostasis in animals and humans, and their activity in cellular differentiation has also been established, Ostrem et al., Proc. Natl. Acad. Sci. USA, 84, 2610 (1987). Many structural analogs of these metabolites have been prepared and tested, including 1α-hydroxyvitamin $D_3$, 1α-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases such as renal osteodystrophy, vitamin D-resistant rickets, osteoporosis, psoriasis, and certain malignancies.

Another class of vitamin D analogs, i.e. the so called 19-nor-vitamin D compounds, is characterized by the replacement of the A-ring exocyclic methylene group (carbon 19), typical of the vitamin D system, by two hydrogen atoms. Biological testing of such 19-nor-analogs (e.g., 1α,25-dihydroxy-19-nor-vitamin $D_3$) revealed a selective activity profile with high potency in inducing cellular differentiation, and very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Lett. 31, 1823 (1990); Perlman et al., Tetrahedron Lett. 32, 7663 (1991), and DeLuca et al., U.S. Pat. No. 5,086,191).

In U.S. Pat. No. 4,666,634, 2β-hydroxy and alkoxy (e.g., ED-71) analogs of 1α,25-dihydroxyvitamin $D_3$ have been described and examined by Chugai group as potential drugs for osteoporosis and as antitumor agents. See also Okano et al., Biochem. Biophys. Res. Commun. 163, 1444 (1989). Other 2-substituted (with hydroxyalkyl, e.g., ED-120, and fluoroalkyl groups) A-ring analogs of 1α,25-dihydroxyvitamin $D_3$ have also been prepared and tested (Miyamoto et al., Chem. Pharm. Bull. 41, 1111 (1993); Nishii et al., Osteoporosis Int. Suppl. 1, 190 (1993); Posner et al., J. Org. Chem. 59, 7855 (1994), and J. Org. Chem. 60, 4617 (1995)), as have analogs with a cyclopropyl group in the side chain (e.g. MC-903 known as calcipotriene and described in Nishii et al U.S. Pat. No. 5,063,221).

2-substituted analogs of 1α,25-dihydroxy-19-nor-vitamin $D_3$ have also been synthesized, i.e. compounds substituted at 2-position with hydroxy or alkoxy groups (DeLuca et al., U.S. Pat. No. 5,536,713), with 2-alkyl groups (DeLuca et al U.S. Pat. No. 5,945,410), and with 2-alkylidene groups (DeLuca et al U.S. Pat. No. 5,843,928), which exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, analogs which are characterized by the presence of a methylene substituent at carbon 2 (C-2), a hydroxyl group at carbon 1 (C-1), and a shortened side chain attached to carbon 20 (C-20) have also been synthesized and tested. 1α-hydroxy-2-methylene-19-nor-pregnacalciferol is described in U.S. Pat. No. 6,566,352 while 1α-hydroxy-2-methylene-19-nor-homopregnacalciferol is described in U.S. Pat. No. 6,579,861 and 1α-hydroxy-2-methylene-19-nor-bishomopregnacalciferol is described in U.S. Pat. No. 6,627,622. All three of these compounds have relatively high binding activity to vitamin D receptors and relatively high cell differentiation activity, but little if any calcemic activity as compared to 1α,25-dihydroxyvitamin $D_3$. Their biological activities make these compounds excellent candidates for a variety of pharmaceutical uses, as set forth in the '352, '861 and '622 patents.

17-ene vitamin D compounds as well as vitamin D compounds having a double bond in the side chain thereof are also known, and have been proposed for various pharmacological uses. Bone diseases such as osteoporosis, skin disorders such as psoriasis, cancers such as leukemia and cosmetic conditions such as wrinkles are just some of the applications proposed for such compounds. 17-ene compounds are described in U.S. Pat. Nos. 5,545,633; 5,929,056 and 6,399,797 while 2-alkylidene compounds having a side chain with a double bond therein are described in, for example, U.S. Pat. No. 5,843,928.

19-nor vitamin D compounds substituted at the carbon-2 position of ring A with an alkyl group such as methyl, or an alkylidene group such as methylene, and having a side chain lacking one or more of the standard vitamin $D_3$ substitutents, are also known, and have been proposed for various pharmacological uses. For example, numerous 2α-methyl-19,26,27-trinor analogs are described in published U.S. Application No. 2007/028704 and in published U.S. Application No. 2007/0270391, and numerous 2-methylene-19,26,27-trinor analogs are described in published U.S. Application No. 2007/0249567. In addition, 2α-methyl-19-nor-(20S)-1α-hydroxy-bishomopregnacalciferol is described in published U.S. Application No. 2007/0254857.

SUMMARY OF THE INVENTION

The present invention is directed toward (20R)-2α-methyl-19,26,27-trinor-vitamin D analogs, their biological activity, and various pharmaceutical uses for these compounds. These new vitamin D compounds not known heretofore are the 19-nor-vitamin D analogs having a methyl group at the 2-position (C-2), a hydroxyl substituent attached to the 25-position (C-25) in the side chain, and the methyl groups normally located at the 26 and 27 positions (C-26 and C-27) in the side chain replaced with hydrogen atoms. The preferred vitamin D analog is (20R)-2α-methyl-19,26,27-trinor-1α,25-dihydroxyvitamin $D_3$ (hereinafter referred to as "B-9").

Structurally these (20R)-2α-methyl-19,26,27-trinor-vitamin D analogs are characterized by the general formula I shown below:

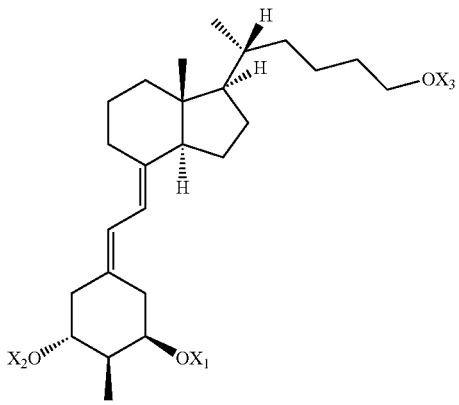

where $X_1$, $X_2$ and $X_3$, which may be the same or different, are each selected from hydrogen or a hydroxy-protecting group. The preferred analog is (20R)-2α-methyl-19,26,27-trinor-1α,25-dihydroxyvitamin $D_3$ which has the following formula Ia:

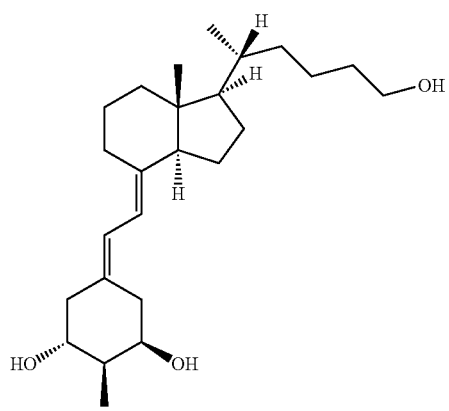

The above compounds I, particularly Ia, exhibit a desired, and highly advantageous, pattern of biological activity. These compounds are characterized by relatively high binding to vitamin D receptors, which is only slightly less than that of the native hormone 1α,25-dihydroxyvitamin $D_3$. These compounds have very little, if any, ability to promote intestinal calcium transport in vivo. They would be classified as having substantially no potency in vivo in stimulating intestinal calcium transport activity, as compared to that of 1α,25-dihydroxyvitamin $D_3$. These compounds I, and particularly Ia, also have very little ability to mobilize calcium from bone, and they would be classified as having substantially no bone calcium mobilizing activity as compared to 1α,25-dihydroxyvitamin $D_3$. It is undesirable to raise serum calcium to supraphysiologic levels when suppressing the preproparathyroid hormone gene (Darwish & DeLuca, Arch. Biochem. Biophys. 365, 123-130, 1999) and parathyroid gland proliferation. These analogs having relatively no bone calcium mobilization activity while very active on cell differentiation are expected to be useful as a therapy for suppression of secondary hyperparathyroidism of renal osteodystrophy.

The compounds I, particularly Ia, of the invention have also been discovered to be especially suited for treatment and prophylaxis of human disorders which are characterized by an imbalance in the immune system, e.g. in autoimmune diseases, including multiple sclerosis, lupus, diabetes mellitus, host versus graft rejection, and rejection of organ transplants; and additionally for the treatment of inflammatory diseases, such as rheumatoid arthritis, asthma, and inflammatory bowel diseases such as celiac disease, ulcerative colitis and Crohn's disease. Acne, alopecia and hypertension are other conditions which may be treated with the compounds of the invention.

The above compounds I, and particularly Ia, are also characterized by relatively high cell differentiation activity and in promoting transcription. Thus, these compounds also provide a therapeutic agent for the treatment of psoriasis, or as an anti-cancer agent, especially against leukemia, colon cancer, breast cancer, skin cancer and prostate cancer. In addition, due to their relatively high cell differentiation activity, these compounds provide a therapeutic agent for the treatment of various skin conditions including wrinkles, lack of adequate dermal hydration, i.e. dry skin, lack of adequate skin firmness, i.e. slack skin, and insufficient sebum secretion. Use of these compounds thus not only results in moisturizing of skin but also improves the barrier function of skin.

The compounds of the invention of formula I, and particularly formula Ia, are also useful in preventing or treating obesity, inhibiting adipocyte differentiation, inhibiting SCD-1 gene transcription, and/or reducing body fat in animal subjects. Therefore, in some embodiments, a method of preventing or treating obesity, inhibiting adipocyte differentiation, inhibiting SCD-1 gene transcription, and/or reducing body fat in an animal subject includes administering to the animal subject, an effective amount of one or more of the compounds or a pharmaceutical composition that includes one or more of the compounds of formula I. Administration of one or more of the compounds or the pharmaceutical compositions to the subject inhibits adipocyte differentiation, inhibits gene transcription, and/or reduces body fat in the animal subject.

One or more of the compounds may be present in a composition to treat the above-noted diseases and disorders in an amount from about 0.01 μg/gm to about 1000 μg/gm of the composition, preferably from about 0.1 μg/gm to about 500 μg/gm of the composition, and may be administered topically, transdermally, orally, rectally, nasally, sublingually or parenterally in dosages of from about 0.01 μg/day to about 1000 μg/day, preferably from about 0.1 μg/day to about 500 μg/day.

BRIEF DESCRIPTION OF THE DRAWINGS

In the drawings:

FIG. 1 is a graph illustrating the relative activity of B-9 and 1,25(OH)-$_2D_3$ to compete for binding with [$^3$H]-1,25-$(OH)_2$-$D_3$ to the full-length recombinant rat vitamin D receptor;

FIG. 2 is a graph illustrating the percent HL-60 cell differentiation as a function of the concentration of B-9 and 1,25 $(OH)_2D_3$;

FIG. 3 is a graph illustrating the in vitro transcription activity of 1,25$(OH)_2D_3$ as compared to B-9;

FIG. 4 is a graph illustrating the bone calcium mobilization activity of 1,25$(OH)_2D_3$ as compared to B-9 in a group of animals; and FIG. 5 is a graph illustrating the intestinal calcium transport activity of 1,25$(OH)_2D_3$ as compared to B-9 in a group of animals.

Figure 1:
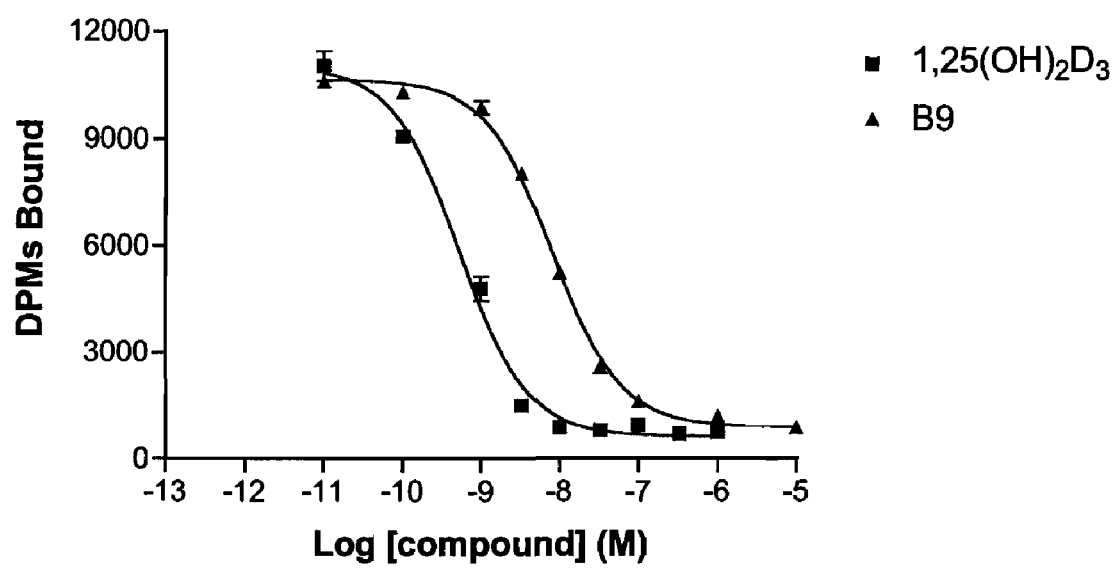
FIGS. 1-5 illustrate various biological activities of (20R)-2α-methyl-19,26,27-trinor-1α,25-dihydroxyvitamin $D_3$, hereinafter referred to as "B-9", as compared to the native hormone 1α,25-dihydroxyvitamin $D_3$, hereinafter "1,25 $(OH)_2D_3$."

DETAILED DESCRIPTION OF THE INVENTION (20R)-1α-methyl-19,26,27-trinor-1α,25-dihydroxyvitamin $D_3$ (referred to herein as "B-9") a 19-nor vitamin D analog which is characterized by the presence of a methyl substituent at the carbon 2 (C-2), a hydroxyl substituent attached to the 25-position (C-25) in the side chain, and the methyl groups normally located at the 26 and 27 positions (C-26 and C-27) in the side chain replaced with hydrogen atoms, was synthesized and tested. Such vitamin D analog seemed an interesting target because the relatively small methyl group at the C-2 position should not interfere with binding to the vitamin D receptor. Structurally, this 19-nor analog is characterized by the general formula Ia previously illustrated herein, and its pro-drug (in protected hydroxy form) is characterized by general formula I previously illustrated herein.

The preparation of (20R)-2α-methyl-19,26,27-trinor-vitamin D analogs having the structure I can be accomplished by a common general method, i.e. the condensation of a bicyclic Windaus-Grundmann type ketone II with the allylic phosphine oxide III to the corresponding 2-methylene-19-nor-vitamin D analog IV followed by deprotection at C-1, C-3 and C-25 in the latter compound (see Scheme III herein):

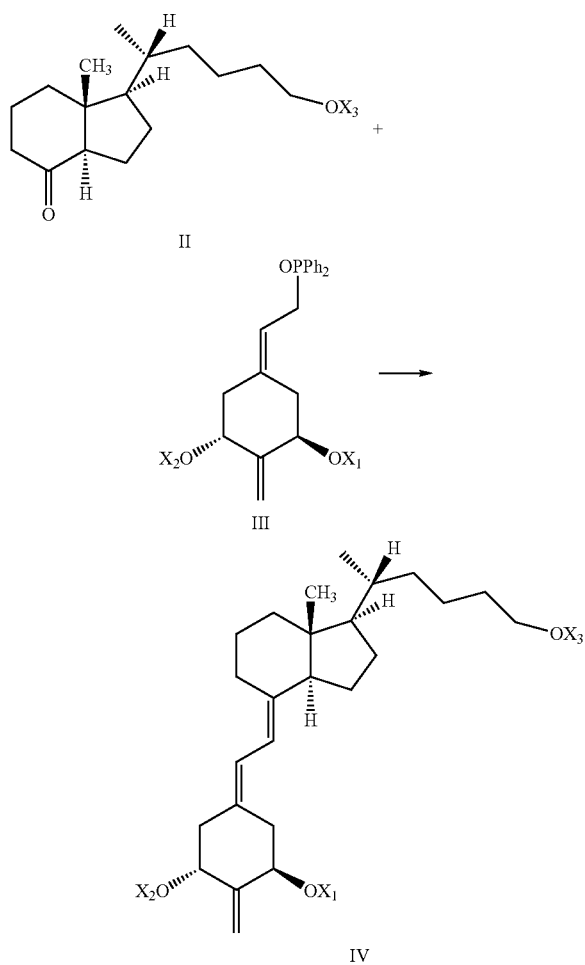

Thereafter, the 2-methylene substituent is converted to a mixture of the 2α-methyl and 2β-methyl epimers, and finally the 2α-methyl analog Ia may be separated and obtained from the mixture by reversed-phase HPLC. In the structures II, III and IV, groups $X_1$, $X_2$ and $X_3$ are hydroxy-protecting groups, preferably t-butyldimethylsilyl, it being also understood that any functionalities that might be sensitive, or that interfere with the condensation reaction, be suitably protected as is well-known in the art. The process shown above represents an application of the convergent synthesis concept, which has been applied effectively for the preparation of vitamin D compounds [e.g. Lythgoe et al., J. Chem. Soc. Perkin Trans. I, 590 (1978); Lythgoe, Chem. Soc. Rev. 9, 449 (1983); Toh et al., J. Org. Chem. 48, 1414 (1983); Baggiolini et al., J. Org. Chem. 51, 3098 (1986); Sardina et al., J. Org. Chem. 51, 1264 (1986); J. Org. Chem. 51, 1269 (1986); DeLuca et al., U.S. Pat. No. 5,086,191; DeLuca et al., U.S. Pat. No. 5,536,713].

The hydrindanone of the general structure II is not known. It can be prepared by the method shown in Schemes I and II herein (see the preparation of compound B-9).

For the preparation of the required phosphine oxides of general structure III, a synthetic route has been developed starting from a methyl quinicate derivative which is easily obtained from commercial (1R,3R,4S,5R)-(−)-quinic acid as described by Perlman et al., Tetrahedron Lett. 32, 7663 (1991) and DeLuca et al., U.S. Pat. No. 5,086,191.

The overall process of the synthesis of compounds I and Ia is illustrated and described more completely in U.S. Pat. No. 5,945,410 entitled "2-Alkyl-19-Nor-Vitamin D Compounds" the specification of which is specifically incorporated herein by reference.

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively.

More specifically, reference should be made to the following illustrative example and description as well as to Schemes I, II and III herein for a detailed illustration of the preparation of compound B-9.

In this example specific products identified by Arabic numerals (1, 2, 3) refer to the specific structures so identified in the Schemes I, II, and III.

EXAMPLE

Chemistry. Ultraviolet (UV) absorption spectra were recorded with a Hitachi Model 60-100 UV-vis spectrometer in the solvent noted. $^1$H nuclear magnetic resonance (NMR) spectra were recorded at 500 MHz with a Bruker AM-500 FT spectrometer in deuteriochloroform. Chemical shifts ($\delta$) are reported downfield from internal Me$_4$Si ($\delta$ 0.00). Mass spectra were recorded at 70 eV on a Kratos DS-50 TC instrument equipped with a Kratos MS-55 data system. Samples were introduced into the ion source maintained at 120-250° C. via a direct insertion probe. High-performance liquid chromatography (HPLC) was performed on a Waters Associates liquid chromatograph equipped with a Model 6000A solvent delivery system, a Model 6 UK Universal injector, a Model 486 tunable absorbance detector, and a differential R 401 refractometer.

Example 1

Preparation of (8S,20S)-de-A,B-20-(hydroxymethyl)-pregnan-8-ol (1). Ozone was passed through a solution of vitamin D$_2$ (3 g, 7.6 mmol) in methanol (250 mL) and pyridine (2.44 g, 2.5 mL, 31 mmol) for 50 min at −78° C. The reaction mixture was then flushed with an oxygen for 15 min to remove the residual ozone and the solution was treated with NaBH$_4$ (0.75 g, 20 mmol). After 20 min the second portion of NaBH$_4$ (0.75 g, 20 mmol) was added and the mixture was allowed to warm to room temperature. The third portion of NaBH$_4$ (0.75 g, 20 mmol) was then added and the reaction mixture was stirred for 18 h. The reaction was quenched with water (40 mL) and the solution was concentrated under reduced pressure. The residue was extracted with ethyl acetate (3×80 mL) and the combined organic phase was washed with 1M aq. HCl, saturated aq. NaHCO$_3$, dried (Na$_2$SO$_4$) and concentrated under reduced pressure. The residue was chromatographed on silica gel with hexane/ethyl acetate (75:25) to give the diol 1 (1.21 g, 75% yield) as white crystals.

m.p. 106-108° C.; $[\alpha]_D$+30.2° (c 1.46, CHCl$_3$); $^1$H NMR (400 MHz, CDCl$_3$) $\delta$ 4.08 (1H, d, J=2.0 Hz, 8$\alpha$-H), 3.63 (1H, dd, J=10.5, 3.1 Hz, 22-H), 3.38 (1H, dd, J=10.5, 6.8 Hz, 22-H), 1.99 (1H, br.d, J=13.2 Hz), 1.03 (3H, d, J=6.6 Hz, 21-H$_3$), 0.956 (3H, s, 18-H$_3$); $^{13}$C NMR (100 MHz) $\delta$ 69.16 (d, C-8), 67.74 (t, C-22), 52.90 (d), 52.33 (d), 41.83 (s, C-13), 40.19 (t), 38.20 (d), 33.53 (t), 26.62 (t), 22.54 (t), 17.36 (t), 16.59 (q, C-21), 13.54 (q, C-18); MS (EI) m/z 212 (2, M$^+$), 194 (34, M$^+$-H$_2$O), 179 (33, M$^+$-H$_2$O—CH$_3$), 163 (18, M$^+$-CH$_2$OH—H$_2$O), 135 (36), 125 (54), 111 (100), 95 (63), 81 (67); exact mass calculated for C$_{13}$H$_{22}$O (M$^+$-H$_2$O) 194.1671, found 194.1665.

Preparation of (8S,20S)-de-A,B-20-(acetyloxymethyl)-pregnan-8-ol (2). Acetic anhydride (1.05 mL, 1.13 g, 11.1 mmol) was added to a solution of the diol 1 (1.8 g, 8.5 mmol) and triethylamine (4.2 mL, 3.03 g, 30 mmol) in anhydrous dichloromethane (10 mL) at 0° C. The mixture was stirred under argon at room temperature for 18 h. The reaction was quenched with water (10 mL) and extracted with dichloromethane. The combined organic phase was washed with brine, dried (Na$_2$SO$_4$) and concentrated under reduced pressure. The pure alcohol 2 (2.09 g, 97% yield) was isolated by a chromatography on silica gel with hexane/ethyl acetate (95:5, then 9:1), as a colorless oil:

$[\alpha]_D$+34.4° (c 1.63, CHCl$_3$); $^1$H NMR (500 MHz, CDCl$_3$+TMS) $\delta$ 4.09 (1H, s, 8$\alpha$-H), 4.07 (1H, dd, J=10.7, 3.5 Hz, 22-H), 3.78 (1H, dd, J=10.7, 7.5 Hz, 22-H), 2.05 (3H, s, CO Me), 1.99 (1H, dm, J=12.8 Hz), 1.00 (3H, d, J=6.6 Hz, 21-H$_3$), 0.96 (3H, s, 18-H$_3$); $^{13}$C NMR (125 MHz) $\delta$ 171.35 (s, C=O), 69.39 (t, C-22), 69.07 (d, C-8), 53.21 (d), 52.30 (d), 41.91 (s, C-13), 40.19 (t), 35.30 (d), 33.54 (t), 26.60 (t), 22.53 (t), 20.95 (q, COMe), 17.36 (t), 16.97 (q, C-21), 13.50 (q, C-18); MS (EI) m/z 254 (10, M$^+$), 236 (24, M$^+$-H$_2$O), 212 (9, M$^+$-C$_2$H$_2$O), 194 (67, M$^+$-CH$_3$COOH), 176 (91, M$^+$-CH$_3$COOH—H$_2$O), 161 (83), 150 (80), 135 (91), 125 (97), 112 (98), 97 (100); exact mass calculated for C$_{15}$H$_{24}$O$_2$ (M$^+$-H$_2$O) 235.1776, found 236.1771.

Preparation of (8S,20S)-de-A,B-8-triethylsilyloxy-20-(acetyloxymethyl)-pregnane (3). Triethylsilyl trifluoromethanesulfonate (1.9 mL, 2.24 g, 8.5 mmol) was added to a solution of the alcohol 2 (2.08 g, 8.2 mmol) and 2,6-lutidine (2.86 mL, 2.63 g, 24.6 mmol) in anhydrous dichloromethane (10 mL) at 0° C. The mixture was stirred under argon at 0° C. for 0.5 h. The reaction was quenched with water (30 mL) and extracted with dichloromethane. The combined organic phase was washed with water, dried (Na$_2$SO$_4$) and concentrated under reduced pressure. The product 3 (2.9 g, 96% yield) was isolated by a chromatography on silica gel with hexane/ethyl acetate (95:5), as a colorless oil:

$[\alpha]_D$+40.8° (c 1.95, CHCl$_3$); $^1$H NMR (400 MHz, CDCl$_3$) $\delta$ 4.06 (1H, dd, J=10.7, 3.4 Hz, 22-H), 4.04 (1H, s, 8$\alpha$-H), 3.77 (1H, dd, J=10.7, 7.6 Hz, 22-H), 2.04 (3H, s, COMe), 1.93 (1H, dm, J=12.4 Hz), 0.98 (3H, d, J=6.6 Hz, 21-H$_3$), 0.94 (9H, t, J=7.9 Hz, Si(CH$_2$CH$_3$)$_3$), 0.92 (3H, s, 18-H$_3$), 0.55 (6H, q, J=7.9 Hz, Si(CH$_2$CH$_3$)$_3$); $^{13}$C NMR (100 MHz) $\delta$ 171.39 (s, C=O), 69.57 (t, C-22), 69.22 (d, C-8), 53.41 (d), 52.81 (d), 42.22 (s, C-13), 40.60 (t), 35.36 (d), 34.59 (t), 26.77 (t), 23.04 (t), 20.99 (q, COMe), 17.64 (t), 17.05 (q, C-21), 13.53 (q, C-18), 6.92 (q, SiCH$_2$CH$_3$), 4.93 (t, SiCH$_2$CH$_3$); MS (EI) m/z 368 (29, M$^+$), 339 (85, M$^+$-C$_2$H$_5$), 325 (78, M$^+$-CH$_3$CO), 265 (31, M$^+$-CH$_3$COOC$_3$H$_7$—H), 237 (21, M$^+$-Et$_3$SiO), 217 (88), 189 (72), 177 (92), 161 (77), 145 (93), 135 (98), 121 (90), 107 (91), 95 (100); exact mass calculated for C$_{19}$H$_{35}$O$_3$Si (M$^+$-C$_2$H$_5$) 339.2355, found 339.2352.

Preparation of (8S,20S)-de-A,B-8-triethylsilyloxy-20-(hydroxymethyl)-pregnane (4). A solution of sodium hydroxide (1.5 g, 37.5 mmol) in anhydrous ethanol (20 mL) was added to a mixture of the compound 3 (2.9 g, 7.9 mmol) in anhydrous ethanol (10 mL). The reaction mixture was stirred at room temperature for 30 min. and then neutralized with 5% aq. hydrochloric acid. The mixture was extracted with dichloromethane and the combined organic phases were washed with water, dried (Na$_2$SO$_4$) and concentrated under reduced pressure. The residue was chromatographed on silica gel with hexane/ethyl acetate (95:5, then 9:1) to give the alcohol 4 (2.58 g, 100% yield):

$[\alpha]_D$+38.9° (c 2.45, CHCl$_3$); $^1$H NMR (500 MHz, CDCl$_3$) $\delta$ 4.07 (1H, d, J=2.3 Hz, 8$\alpha$-H), 3.66 (1H, dd, J=10.5, 3.2, Hz, 22-H), 3.39 (1H, dd, J=10.5, 6.8 Hz, 22-H), 1.98 (1H, dm, J=12.7 Hz), 1.05 (3H, d, J=6.6 Hz, 21-H$_3$), 0.98 (9H, t, J=7.9 Hz, Si(CH$_2$CH$_3$)$_3$), 0.95 (3H, s, 18-H$_3$), 0.58 (6H, q, J=7.9 Hz, Si(CH$_2$CH$_3$)$_3$); $^{13}$C NMR (125 MHz) $\delta$ 69.26 (d, C-8), 67.97 (t, C-22), 53.10 (d), 52.86 (d), 42.14 (s, C-13), 40.63 (t), 38.28 (d), 34.60 (t), 26.80 (t), 23.05 (t), 17.64 (t), 16.65 (q, C-21), 13.56 (q, C-18), 6.91 (q, SiCH$_2$CH$_3$), 4.92 (t, SiCH$_2$CH$_3$); MS (EI) m/z 326 (58, M$^+$), 311 (15, M$^+$-CH$_3$), 297 (93, M$^+$-C$_2$H$_5$), 283 (89, M$^+$-C$_2$H$_2$O), 225 (80), 211 (24, M$^+$-Et$_3$Si), 193 (90), 177 (98), 135 (98), 121 (99), 107 (99), 95 (100); exact mass calculated for C$_{19}$H$_{38}$O$_2$Si (M$^+$) 326.2641, found 326.2549.

Preparation of (8S,20S)-de-A,B-8-triethylsilyloxy-20-(iodomethyl)-pregnane (5). A solution of iodine (1.52 g, 6 mmol) in methylene chloride (120 mL) was slowly added to a solution of triphenylphosphine (1.6 g, 6.1 mmol) and imidazole (816 mg, 12 mmol) in methylene chloride (10 mL) at 0° C. After 15 min. a solution of alcohol 4 (0.5 g, 1.5 mmol) in methylene chloride (10 mL) was added, the mixture was stirred at 0° C. for 20 min. and at room temperature for 18 h. The reaction mixture was washed with water, dried ($Na_2SO_4$) and concentrated under reduced pressure. The residue was chromatographed on silica gel with hexane to give the desired iodide 5 (657 mg, 100%):

$[\alpha]_D$+52.0° (c 1.44, $CHCl_3$); $^1H$ NMR (400 MHz, $CDCl_3$) δ 4.04 (1H, d, J=2.1 Hz, 8α-H), 3.33 (1H, dd, J=9.5, 2.3 Hz, 22-H), 3.17 (1H, dd, J=9.5, 5.3 Hz), 1.90 (1H, dm, J=12.5 Hz), 0.99 (3H, d, J=5.9 Hz, 21-$H_3$), 0.95 (9H, t, J=7.9 Hz, Si($CH_2CH_3$)$_3$), 0.95 (3H, s, 18-$H_3$), 0.55 (6H, q, J=7.9 Hz, Si($CH_2CH_3$)$_3$); $^{13}C$ NMR (100 MHz) δ 69.25 (d, C-8), 56.03 (d), 52.80 (d), 42.10 (s, C-13), 40.46 (t), 36.46 (d), 34.50 (t), 26.66 (t), 22.85 (t), 21.61 (t), 20.71 (q, C-21), 17.61 (t), 14.34 (q, C-18), 6.94 (q, $SiCH_2CH_3$), 4.93 (t, $SiCH_2CH_3$); MS (EI) m/z 436 (42, $M^+$), 421 (3, $M^+$-$CH_3$), 407 (95, $M^+$-$C_2H_9$), 393 (76), 309 (23, $M^+$-I), 303 (86, $M^+$-$Et_3$SiOH—H), 251 (28), 225 (35), 177 (96), 135 (96), 121 (87), 95 (97), 75 (100); exact mass calculated for $C_{19}H_{37}OSiI$ ($M^+$) 436.1658, found 436.1645.

Preparation of (8S,20R)-de-A,B-8-triethylsilyloxy-20-(3-isopropoxycarbonyl)-propyl-pregnane (6). A mixture of zinc powder (488 mg, 7.5 mmol), anhydrous pyridine (8 mL) and isopropyl acrylate (900 μL, 855 mg, 7.5 mmol) was warmed to 50° C., then nickel(II) chloride hexahydrate (428 mg, 1.8 mmol) was added. The resulting mixture was warmed to 65° C. and stirred for 2 h until its green color turned to reddish brown one. After cooling to 0° C., a solution of iodide 5 (657 mg, 1.5 mmol) in anhydrous pyridine (6 mL) was added and the reaction mixture was stirred for 7 h at room temperature. The mixture was diluted with ethyl acetate (20 mL) and the resulting precipitate was filtered off through a pad of Celite. The filtrate was washed with 5% aq. HCl and brine, dried ($Na_2SO_4$) and concentrated under reduced pressure. The residue was chromatographed on silica gel with hexane and hexane/ethyl acetate (95:5) to give the ester 6 (494 mg, 78%): $[\alpha]_D$+41.8° (c 1.41, $CHCl_3$); $^1H$ NMR (500 MHz, $CDCl_3$) δ 4.99 (1H, sep, J=6.3 Hz, $OCHMe_2$), 4.01 (1H, s, 8α-H), 2.22 (2H, m, 24-$H_2$), 1.93 (1H, dm, J=12.2 Hz), 1.22 (6H, d, J=6.3 Hz, $OCHMe_2$), 0.93 (9H, t, J=7.9 Hz, Si($CH_2CH_3$)$_3$), 0.89 (3H, d, J=5.6 Hz, 21-$H_3$), 0.88 (3H, s, 18-$H_3$), 0.54 (6H, q, J=7.9 Hz, Si($CH_2CH_3$)$_3$); $^{13}C$ NMR (125 MHz) δ 173.44 (s, COO-iPr), 69.37 (d, C-8), 67.26 (d, $COOCHMe_2$), 56.50 (d), 53.06 (d), 42.09 (s, C-13), 40.74 (t), 35.20 (t), 35.13 (t), 35.01 (d), 34.63 (t), 27.25 (t), 22.98 (t), 21.84 (q, $COOCHMe_2$), 21.58 (t), 18.52 (q, C-21), 17.66 (t), 13.46 (q, C-18), 6.92 (q, $SiCH_2CH_3$), 4.91 (t, $SiCH_2CH_3$); MS (EI) m/z 424 (35, $M^+$), 409 (6, $M^+$-$CH_3$), 395 (87, $M^+$-$C_2H_9$), 381 (39, $M^+$-$C_3H_7$), 365 (41, $M^+$-$C_3H_7O$), 335 (90, $M^+$-$C_3H_7COOH$—H), 295 (29), 249 (26), 225 (64), 215 (54), 199 (33), 171 (29), 135 (88), 115 (55), 103 (100); exact mass calculated for $C_{25}H_{48}O_3Si$ ($M^+$) 424.3373, found 424.3373.

Preparation of (8S,20R)-de-A,B-8-triethylsilyloxy-20-(4-hydroxy-butyl)-pregnane (7). Lithium aluminium hydride (19 mg, 0.5 mmol) was added to a solution of ester 6 (100 mg, 0.24 mmol) in anhydrous THF (8 mL) at 0° C. A cooling bath was removed and the reaction mixture was stirred for 18 h at room temperature. The excess hydride was quenched by careful, successive addition of methanol. A saturated aq. solution of the tartaric acid was added and the mixture was extracted with methylene chloride. The combined organic phase was washed with water, dried ($Na_2SO_4$) and concentrated under reduced pressure. The residue was chromatographed on silica gel with hexane/ethyl acetate (95:5) to give the alcohol 7 (87 mg, 99%):

$[\alpha]_D$+46.7° (c 0.78, $CHCl_3$); $^1H$ NMR (500 MHz, $CDCl_3$) δ 4.02 (1H, d, J=2.0 Hz, 8α-H), 3.63 (2H, t, J=6.6 Hz, 25-$H_2$), 1.95 (1H, dm, J=12.6 Hz), 0.95 (9H, t, J=7.9 Hz, Si($CH_2CH_3$)$_3$), 0.90 (3H, s, 18-$H_3$), 0.89 (3H, d, J=7.9 Hz, 21-$H_3$), 0.55 (6H, q, J=7.9 Hz, Si($CH_2CH_3$)$_3$); $^{13}C$ NMR (125 MHz) δ 69.38 (d, C-8), 63.07 (t, C-25), 56.68 (d), 53.08 (d), 42.09 (s, C-13), 40.77 (t), 35.54 (t), 35.20 (d), 34.63 (t), 33.26 (t), 27.29 (t), 22.98 (t), 22.17 (t), 18.53 (q, C-21), 17.67 (t), 13.47 (q, C-18), 6.91 (q, $SiCH_2CH_3$), 4.91 (t, $SiCH_2CH_3$); MS (EI) m/z 368 (8, $M^+$), 353 (4, $M^+$-$CH_3$), 339 (56, $M^+$-$C_2H_7$), 325 (53), 297 (18), 283 (13), 225 (54), 177 (37), 163 (69), 135 (93), 103 (100); exact mass calculated for $C_{20}H_{39}O_2Si$ ($M^+$-$C_2H_5$) 399.2719, found 339.2713.

Preparation of (8S,20R)-de-A,B-20-(4-hydroxy-butyl)-pregnan-8-ol (8). To a solution of compound 7 (86 mg, 0.23 mmol) in tetrahydrofuran (2 mL) and acetonitrile (2 mL) a mixture of aq. 48% HF/acetonitrile (1:9 ratio, 2 mL) was added at 0° C. and the resulting mixture was stirred at room temperature for 1 h. Saturated aq. $NaHCO_3$ solution was added and the reaction mixture was extracted with ethyl acetate. The combined organic phase was washed with brine, dried ($Na_2SO_4$) and concentrated under reduced pressure. The residue was chromatographed on silica gel with hexane/ethyl acetate (9:1) to give the diol 8 (60 mg, 100%):

$[\alpha]_D$+40.2° (c 3.05, $CHCl_3$); $^1H$ NMR (500 MHz, $CDCl_3$) δ 4.06 (1H, d, J=2.3 Hz, 8α-H), 3.62 (2H, t, J=6.6 Hz, 25-$H_2$), 1.99 (1H, dm, J=13.0 Hz), 0.92 (3H, s, 18-$H_3$), 0.90 (3H, d, J=6.5 Hz, 21-$H_3$); $^{13}C$ NMR (125 MHz) δ 69.28 (d, C-8), 62.89 (t, C-25), 56.47 (d), 52.53 (d), 41.75 (s, C-13), 40.30 (t), 35.45 (t), 35.14 (d), 33.46 (t), 33.16 (t), 27.10 (t), 22.44 (t), 22.13 (t), 18.42 (q, C-21), 17.36 (t), 13.43 (q, C-18); MS (EI) m/z 254 (7, $M^+$), 236 (8, $M^+$-$H_2O$), 221 (7, $M^+$-$H_2O$—$CH_3$), 163 (8, $M^+$-$H_2O$—$C_4H_8OH$), 135 (25, $M^+$-$H_2O$—$C_6H_{12}OH$), 125 (35), 111 (100), 97 (30); exact mass calculated for $C_{16}H_{30}O$ ($M^+$) 254.2246, found 254.2450.

Preparation of (8S,20R)-de-A,B-20-[4-(tert-butyldimethylsilyloxy)-butyl]-pregnan-8-ol (9). tert-Butyldimethylsilyl chloride (47 mg, 0.31 mmol) was added to a solution of the diol 8 (60 mg, 0.23 mmol) and triethylamine (134 μL, 97 mg, 0.96 mmol) in anhydrous methylene chloride (4 mL). The mixture was stirred under argon at room temperature for 18 h. The reaction was quenched with water and extracted with ethyl acetate. The combined organic phase was washed with brine, dried ($Na_2SO_4$) and concentrated under reduced pressure. The residue was chromatographed on silica gel with hexane and hexane/ethyl acetate (98:2) to give the alcohol 9 (84 mg, 100%):

$[\alpha]_D$+30.1° (c 3.8, $CHCl_3$); $^1H$ NMR (500 MHz, $CDCl_3$) δ 4.05 (1H, d, J=2.2 Hz, 8α-H), 3.58 (2H, t, J=6.6 Hz, 25-$H_2$), 1.98 (1H, dm, J=12.8 Hz), 0.92 (3H, s, 18-$H_3$), 0.88 (3H, d, 21-$H_3$) covered by 0.88 (9H, s, Si-t-Bu), 0.04 (6H, s, $SiMe_2$); $^{13}C$ NMR (125 MHz) δ 69.36 (d, C-8), 63.24 (t, C-25), 56.65 (d), 52.60 (d), 41.82 (s, C-13), 40.38 (t), 35.46 (t), 35.20 (d), 33.57 (t), 33.29 (t), 27.13 (t), 25.95 (q, $SiCMe_3$), 22.49 (t), 22.16 (t), 18.44 (q, C-21), 18.33 (s, $SiCMe_3$), 17.41 (t), 13.49 (q, C-18), −5.28 (q, $SiMe_2$); MS (EI) m/z no $M^+$, 311 (1, $M^+$-$C_4H_9$), 293 (3, $M^+$-$C_4H_9$—$H_2O$), 251 (9, $M^+$-t-$BuSiMe_2H$—H), 219 (32, $M^+$-$H_2O$-t-$BuSiMe_2O$), 163 (54), 149 (30), 135 (55), 123 (63), 109 (100), 95 (76); exact mass calculated for $C_{18}H_{35}O_2Si$ ($M^+$-$C_4H_9$) 311.2406, found 311.2399.

Preparation of (20R)-de-A,B-20-[4-(tert-butyldimethylsilyloxy)-butyl]-pregnan-8-one (10). Pyridinium dichromate (127 mg, 0.34 mmol) was added to a solution of the alcohol 9 (26 mg, 71 μmol) and pyridinium p-toluenesulfonate (3 mg, 12 μmol) in anhydrous methylene chloride (6 mL). The resulting suspension was stirred at room temperature for 3 h. The reaction mixture was filtered through a Waters silica Sep-Pak cartridge (5 g) that was further washed with methylene chloride. After removal of solvents the ketone 10 (23 mg, 89% yield) was obtained as a colorless oil:

$[α]_D$+3.8° (c 1.5, CHCl$_3$); $^1$H NMR (400 MHz, CDCl$_3$) δ 3.59 (2H, t, J=6.4 Hz, 25-H$_2$), 2.43 (1H, dd, J=11.6, 7.5 Hz), 0.94 (3H, d, J=6.1 Hz, 21-H$_3$), 0.885 (9H, s, Si-t-Bu), 0.626 (3H, s, 18-H$_3$), 0.039 (6H, s, SiMe$_2$); $^{13}$C NMR (100 MHz) δ 212.14 (s, C-8), 63.16 (t, C-25), 61.97 (d), 56.65 (d), 49.90 (s, C-13), 40.95 (t), 38.96 (t), 35.43 (d and t), 33.20 (t), 27.48 (t), 25.95 (q, SiCMe$_3$), 24.05 (t), 22.16 (t), 19.03 (t), 18.62 (q, C-21), 18.33 (s, SiCMe$_3$), 12.45 (q, C-18), −5.27 (q, SiMe$_2$); MS (EI) m/z 367 (1, M$^+$+H), 351 (2, M$^+$-CH$_3$), 309 (66, M$^+$-C$_4$H$_9$), 267 (17), 217 (39, M$^+$-H$_2$O-t-BuSiMe$_2$O), 175 (21), 161 (34), 135 (92), 121 (51), 95 (49), 75 (100); exact mass calculated for C$_{18}$H$_{33}$O$_2$Si (M$^+$-C$_4$H$_9$) 309.2250, found 309.2244.

Preparation of (20R)-2-methylene-19,26,27-trinor-1α,25-dihydroxycalciferol (13). To a solution of phosphine oxide 11 (87 mg, 149 μmol) in anhydrous THF (600 μL) at −20° C. was slowly added PhLi (1.3 M in cyclohexane-ether, 200 μL, 260 μmol) under argon with stirring. The solution turned deep orange. After 30 min the mixture was cooled to −78° C. and a precooled (−78° C.) solution of ketone 10 (18 mg, 49 μmol) in anhydrous THF (200 μL) was slowly added. The mixture was stirred under argon at −78° C. for 3 h and at 0° C. for 18 h. Ethyl acetate was added, and the organic phase was washed with brine, dried (Na$_2$SO$_4$) and evaporated. The residue was dissolved in hexane and applied on a Waters silica Sep-Pak cartridge (2 g). The cartridge was washed with hexane and hexane/ethyl acetate (99.5:0.5) to give 19-norvitamin derivative 12 (32 mg). The Sep-Pak was then washed with hexane/ethyl acetate (96:4) to recover the unchanged C,D-ring ketone 10 (5 mg, 14 μmol), and with ethyl acetate to recover diphenylphosphine oxide 11 (55 mg). The protected vitamin 12 was further purified by HPLC (9.4×250 mm Zorbax Sil column, 4 mL/min) using hexane/2-propanol (99.9:0.1) solvent system. Pure compound 12 (31.55 mg, 88% yield) was eluted at R$_f$=4.09 min as a colorless oil:

UV (in hexane) λ$_{max}$ 262.3, 252.0, 243.6 nm; $^1$H NMR (500 MHz, CDCl$_3$) δ 6.22 and 5.84 (each 1H, each d, J=11.1 Hz, 6- and 7-H), 4.97 and 4.92 (each 1H, each s, =CH$_2$), 4.42 (2H, m, 1β- and 3α-H), 3.61 (2H, t, J=6.5 Hz, 25-H$_2$), 2.82 (1H, dm, J=12.1 Hz, 9β-H), 2.52 (1H, dd, J=13.3, 5.9 Hz, 10α-H), 2.46 (1H, dd, J=12.6, 4.4 Hz, 4α-H), 2.33 (1H, dm, J=13.3 Hz, 10β-H), 2.18 (1H, dd, J=12.6, 8.3 Hz, 4β-H), 1.99 (2H, m), 0.92 (3H, d, J=6.4 Hz, 21-H$_3$), 0.902 (9H, s, Si-t-Bu), 0.899 (9H, s, Si-t-Bu), 0.867 (9H, s, Si-t-Bu), 0.545 (3H, s, 18-H$_3$), 0.082 (3H, s, SiMe), 0.069 (3H, s, SiMe), 0.056 (6H, s, 2×SiMe), 0.052 (3H, s, SiMe), 0.028 (3H, s, SiMe); $^{13}$C NMR (125 MHz) δ 152.99 (s, C-2), 141.26 (s, C-8), 132.70 (s, C-5), 122.43 (d, C-6), 116.10 (d, C-7), 106.25 (t, =CH$_2$), 72.54 and 71.63 (each d, C-1 and C-3), 63.31 (t, C-25), 56.58 (d), 56.29 (d), 47.62 (t), 45.68 (s, C-13), 40.61 (t), 38.56 (t), 36.09 (d), 35.64 (t), 33.32 (t), 28.76 (t), 27.71 (t), 25.99 (q, SiCMe$_3$), 25.84 (q, SiCMe$_3$), 25.78 (q, SiCMe$_3$), 23.45 (t), 22.28 (t), 22.22 (t), 18.76 (q, C-21), 18.38 (s, SiCMe$_3$), 18.25 (s, SiCMe$_3$), 18.16 (s, SiCMe$_3$), 12.06 (q, C-18), −4.86 and −5.09 and −5.23 (each q, 6×SiMe); MS (EI) m/z no M$^+$, 673 (8, M$^+$-C$_4$H$_9$), 628 (2, M$^+$-t-BuMeSiH$_2$), 598 (100, M$^+$-t-BuMe$_2$SiOH), 556 (9), 541 (4), 496 (3), 366 (42), 257 (10), 234 (13), 147 (20); exact mass calculated for C$_{43}$H$_{82}$O$_3$Si$_3$Na (MNa$^+$) 753.5470, found 753.5474.

Protected vitamin 12 (31.54 mg, 43 μmol) was dissolved in THF (3 mL) and acetonitrile (3 mL). A solution of aq. 48% HF in acetonitrile (1:9 ratio, 2 mL) was added at 0° C. and the resulting mixture was stirred at room temperature for 3 h. Saturated aq. NaHCO$_3$ solution was added and the reaction mixture was extracted with ethyl acetate. The combined organic phase was washed with brine, dried (Na$_2$SO$_4$) and concentrated under reduced pressure. The residue was diluted with 2 mL of hexane/ethyl acetate (8:2) and applied on a Waters silica Sep-Pak cartridge (2 g). An elution with hexane/ethyl acetate (8:2) and ethyl acetate gave the crude product 13 (20 mg). The vitamin 13 was further purified by straight phase HPLC [9.4×250 mm Zorbax Sil column, 5 mL/min, hexane/2-propanol (85:15) solvent system, R$_f$=8.75 min.] and later by reverse phase HPLC [9.4×250 mm Zorbax Eclipse XDB-C18 column, 4 mL/min, methanol/water (85:15) solvent system, R$_f$=7.90 min.] to give a colorless oil (13.15 mg, 79% yield):

UV (in EtOH) λ$_{max}$ 262.2, 252.7, 244.2 nm; $^1$H NMR (500 MHz, CDCl$_3$) δ 6.34 and 5.88 (1H and 1H, each d, J=11.1 Hz, 6- and 7-H), 5.10 and 5.08 (each 1H, each s, =CH$_2$), 4.46 (2H, m, 1β- and 3α-H), 3.64 (2H, dd, J=11.8, 6.1 Hz, 25-H$_2$), 2.84 (1H, dd, J=13.1, 4.3 Hz, 10β-H), 2.81 (1H, br d, J=15.2 Hz, 9β-H), 2.56 (1H, dd, J=13.3, 3.0 Hz, 4α-H), 2.32 (1H, dd, J=13.3, 6.0 Hz, 4β-H), 2.27 (1H, dd, J=13.1, 8.5 Hz, 10α-H), 0.92 (3H, d, J=6.3 Hz, 21-H$_3$), 0.542 (3H, s, 18-H$_3$); $^{13}$C NMR (125 MHz) δ 151.95 (s, C-2), 143.37 (s, C-8), 130.42 (s, C-5), 124.19 (d, C-6), 115.28 (d, C-7), 107.70 (t, =CH$_2$), 71.79 and 70.61 (each d, C-1 and C-3), 63.08 (t, C-25), 56.40 (d), 56.30 (d), 45.75 (s, C-13) covered by 45.75 (t), 40.42 (t), 38.13 (t), 36.02 (d), 35.63 (t), 33.23 (t), 28.94 (t), 27.63 (t), 23.47 (t), 22.25 (t), 22.20 (t), 18.75 (q, C-21), 12.06 (q, C-18); MS (EI) m/z 388 (3, M$^+$), 334 (1, M$^+$-3H$_2$O), 318 (9, M$^+$-3H$_2$O—CH$_4$), 272 (9), 252 (27), 250 (28), 239 (8), 196 (99), 194 (100), 160 (12); exact mass calculated for C$_{25}$H$_{40}$O$_3$ (M$^+$) 388.2977, found 388.2961.

Preparation of (20R)-2α-methyl-19,26,27-trinor-1α,25-dihydroxycalciferol (14) and (20R)-2β-methyl-19,26,27-trinor-1α,25-dihydroxycalciferol (15). Tris(triphenylphosphine)rhodium (I) chloride (7 mg, 7.6 μmol) was added to dry benzene (5 mL) presaturated with hydrogen (15 min.). The mixture was stirred at room temperature until a homogeneous solution was formed (25 min). A solution of vitamin 13 (2.9 mg, 7.5 μmol) in dry benzene (3 mL) was then added and the reaction was allowed to proceed under a continuous stream of hydrogen for 4 h. Benzene was removed under vacuum, the residue was redissolved in hexane/ethyl acetate (1:1) and applied on a Waters silica Sep-Pak cartridge (2 g). A mixture of 2-methyl vitamins was eluted with the same solvent system. The compounds were further purified by HPLC (9.4×250 mm Zorbax-Sil column, 5 mL/min) using hexane/2-propanol (85:15) solvent system. The mixture of 2-methyl-19-norvitamins 14 and 15 gave a single peak at R$_f$=8.91 min. Separation of both epimers was achieved by reversed-phase HPLC (9.4×250 mm Zorbax Eclipse XDB-C18 column, 3 mL/min) using methanol/water (85:15) solvent system. 2β-Methyl vitamin 15 (911 μg, 31% yield) was collected at R$_f$=8.71 min. and its 2α-epimer 14 (1.055 mg, 36% yield) at R$_f$=9.27 min:

2α-Methyl analog 14: UV (in EtOH) λ$_{max}$ 260.5, 251.5, 243.5 nm; $^1$H NMR (500 MHz, CDCl$_3$) δ 6.37 and 5.82 (1H and 1H, each d, J=11.1 Hz, 6- and 7-H), 3.96 (1H, m, 1β-H), 3.63 (3H, m, 3α-H and 25-H$_2$), 2.80 (2H, br m, 9β- and 10α-H), 2.60 (1H, dd, J=12.8, 4.4 Hz, 4α-H), 2.22 (1H, br d, J=14.3 Hz, 10β-H), 2.13 (1H, ~t, J~11.3 Hz, 4β-H), 1.132 (3H, d, J=6.8 Hz, 2α-CH$_3$), 0.926 (3H, d, J=6.5 Hz, 21-H$_3$), 0.531 (3H, s, 18-H$_3$); MS (EI) m/z 390 (100, M$^+$), 372 (14, M$^+$-H$_2$O), 357 (4, M$^+$-H$_2$O—CH$_3$), 339 (3, M$^+$-2H$_2$O—CH$_3$), 317 (23, M$^+$-C$_4$H$_8$OH), 289 (76, M$^+$-C$_6$H$_{12}$OH), 271 (45, M$^+$-C$_6$H$_{12}$OH—H$_2$O), 253 (40), 235 (46), 194 (35), 159

(30), 147 (57), 135 (70); exact mass calculated for $C_{25}H_{42}O_3$ ($M^+$) 390.3134, found 390.3121.

2β-Methyl analog 15: UV (in EtOH) $\lambda_{max}$ 260.5, 251.0, 243.5 nm; $^1$H NMR (500 MHz, CDCl$_3$) δ 6.26 and 5.87 (1H and 1H, each d, J=11.2 Hz, 6-H and 7-H), 3.90 (1H, m, 3α-H), 3.65 (2H, dd, J=12.2, 6.4 Hz, 25-H$_2$), 3.50 (1H, m, 1β-H), 3.08 (1H, dd, J=12.9, 4.1 Hz, 10β-H), 2.79 (1H, dd, J=12.2, 4.3 Hz, 9β-H), 2.43 (1H, br d, J=ca. 13.7 Hz, 4α-H), 2.34 (1H, dd, J=13.7, 2.6 Hz, 4β-H), 1.142 (3H, d, J=6.8 Hz, 2β-CH$_3$), 0.930 (3H, d, J=6.4 Hz, 21-H$_3$), 0.543 (3H, s, 18-H$_3$); MS (EI) m/z 390 (100, $M^+$), 372 (17, $M^+$-H$_2$O), 354 (5, $M^+$-2H$_2$O), 339 (3, $M^+$-2H$_2$O—CH$_3$), 317 (21, $M^+$-C$_4$H$_8$OH), 289 (62, $M^+$-C$_6$H$_{12}$OH), 271 (37, $M^+$-C$_6$H$_{12}$OH—H$_2$O), 253 (39), 247 (33), 235 (46), 194 (32), 159 (29), 147 (53), 135 (71); exact mass calculated for $C_{25}H_{42}O_3$ ($M^+$) 390.3134, found 390.3133.

Scheme I

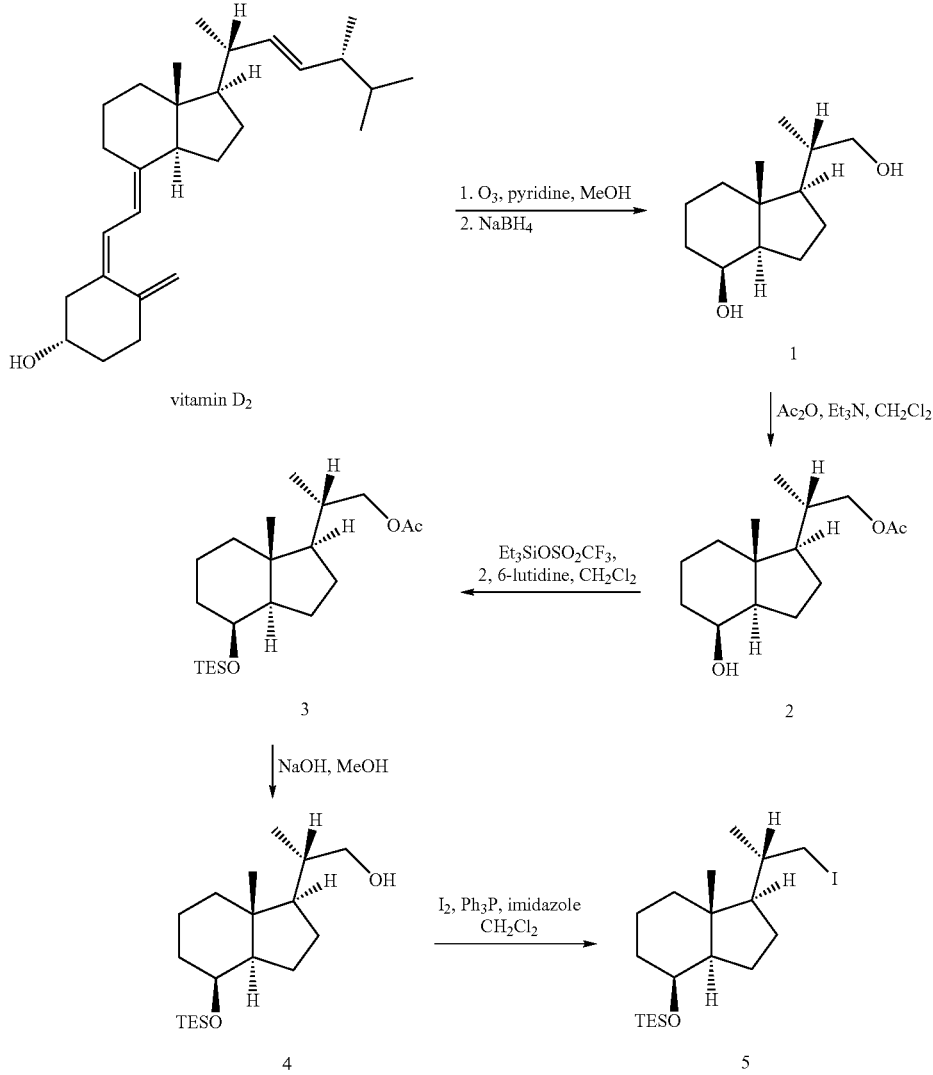

Scheme II

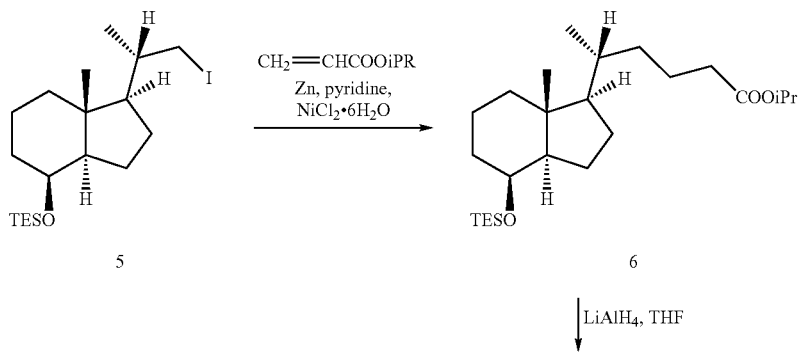

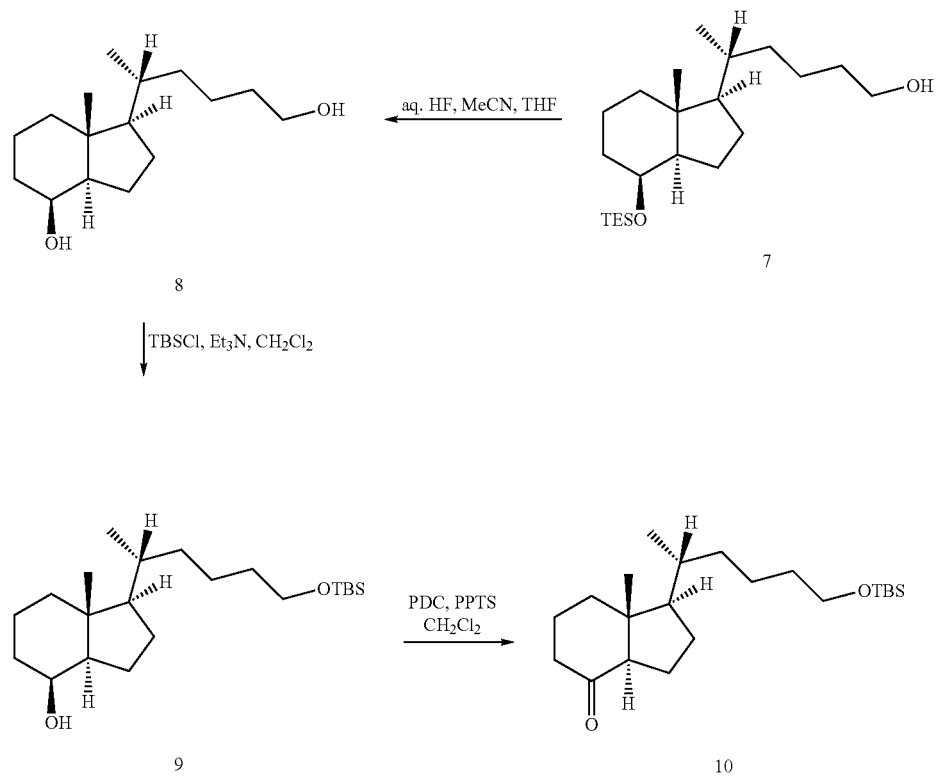
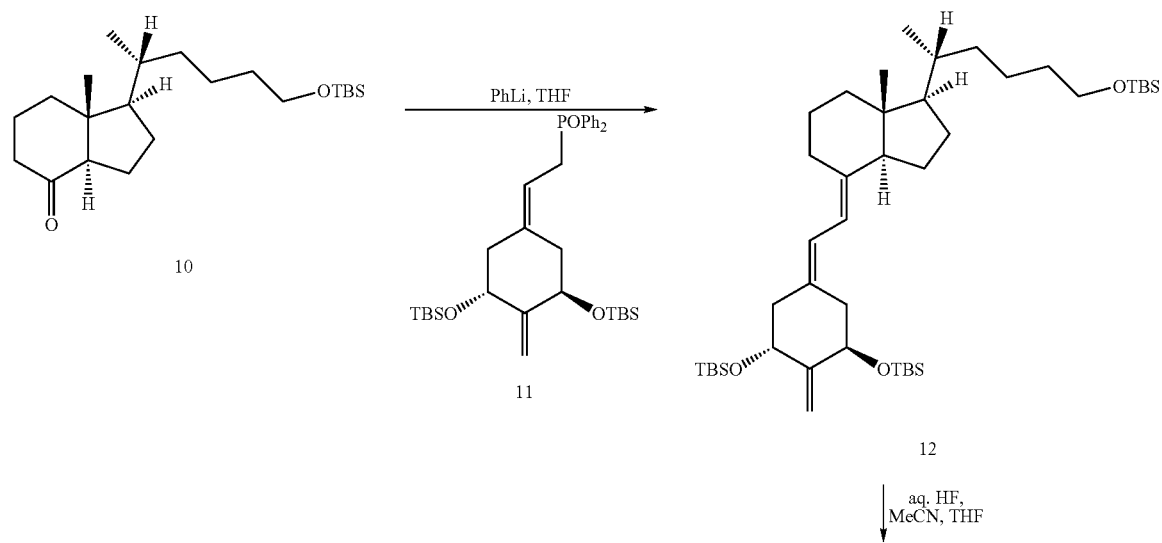
Scheme III

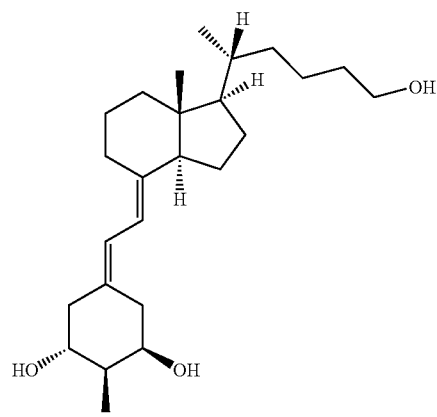

14

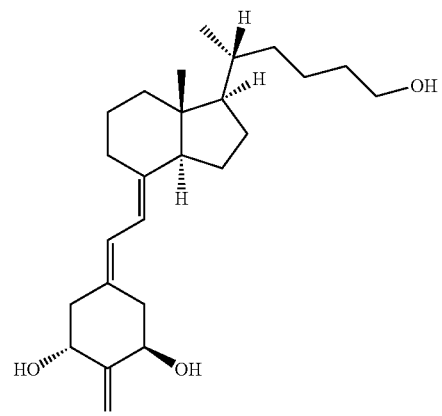

13

1. H₂, (Ph₃P)₃RhCl, benzene
2. HPLC

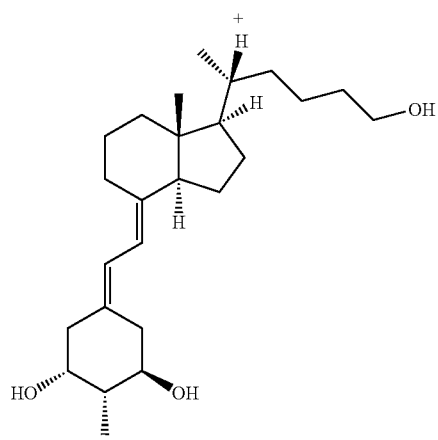

15

Biological Activity of
(20R)-2α-Methyl-19,26,27-Trinor-Vitamin D
Analogs

The introduction of a methyl group to the 2-position, as well as a hydroxyl substituent attached to the 25-position (C-25) in the side chain, and replacing the methyl groups normally located at the 26 and 27 positions (C-26 and C-27) in the side chain with hydrogen atoms bonded to the carbon atom at position 25 in the side chain had a small effect on binding of B-9 to the full length recombinant rat vitamin D receptor, as compared to 1α,25-dihydroxyvitamin $D_3$. The compound B-9 bound with somewhat lower affinity to the nuclear vitamin D receptor as compared to the standard 1,25-$(OH)_2D_3$ (FIG. 1). It might be expected from these results that compound B-9 would have equivalent biological activity. Surprisingly, however, compound B-9 is a highly selective analog with unique biological activity.

Figure 5:
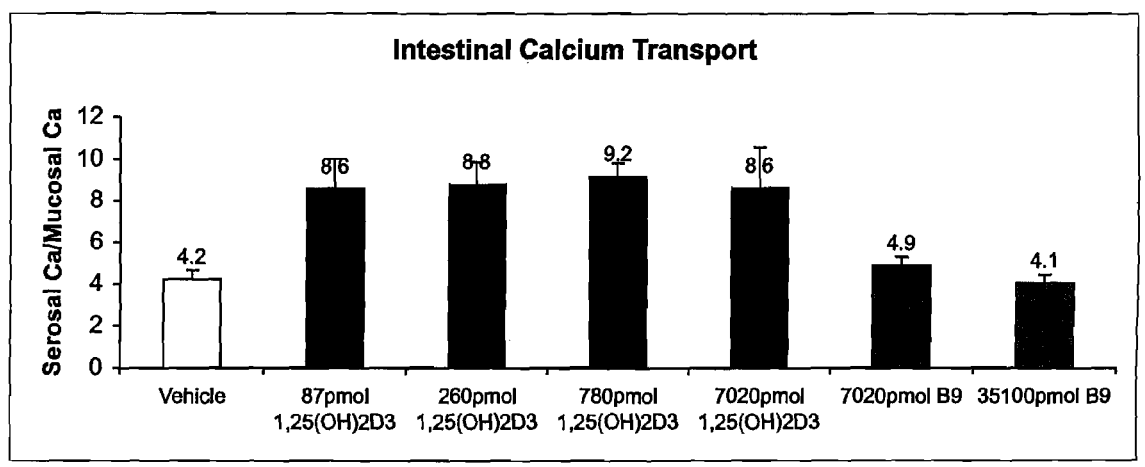

FIG. 5 shows that B-9 has very little, if any, ability to increase intestinal calcium transport activity in vivo, and it clearly has substantially lower potency in vivo as compared to that of 1,25-dihydroxyvitamin $D_3$ (1,25$(OH)_2D_3$), the natural hormone, in stimulating intestinal calcium transport. B-9 did not stimulate intestinal calcium transport even at doses that were about 50 times higher than the dose of 1,25$(OH)_2D_3$.

Figure 4:
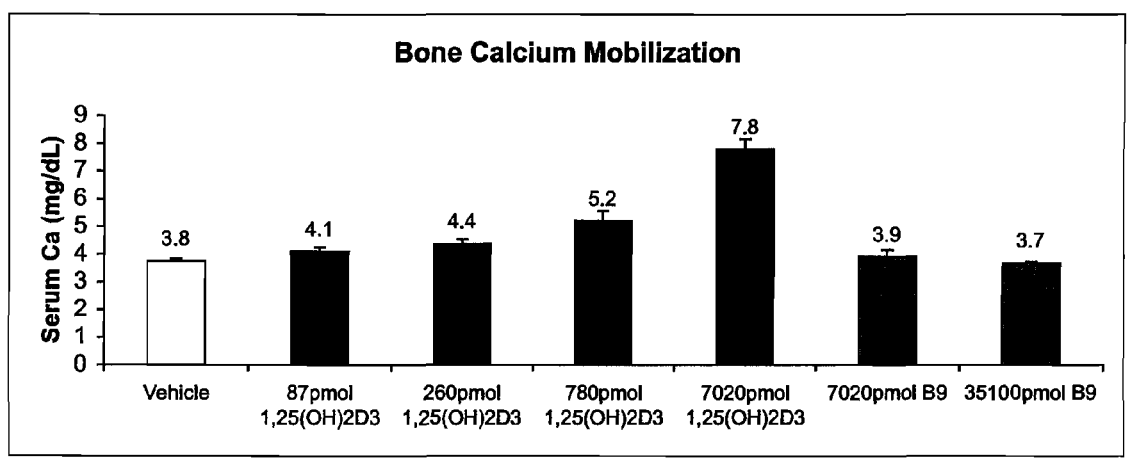

FIG. 4 demonstrates that B-9 has very little, if any, bone calcium mobilization activity, as compared to 1,25$(OH)_2D_3$. B-9 demonstrated no bone calcium mobilization activity even at very high doses that were about 50 times higher than the dose of 1,25$(OH)_2D_3$. Thus, B-9 clearly has significantly lower potency in mobilizing calcium from bone as compared to 1,25$(OH)_2D_3$, at the recommended lower doses.

FIGS. 4 and 5 thus illustrate that B-9 may be characterized as having substantially no intestinal calcium transport activity, and substantially no bone calcium mobilization activity.

Figure 2:
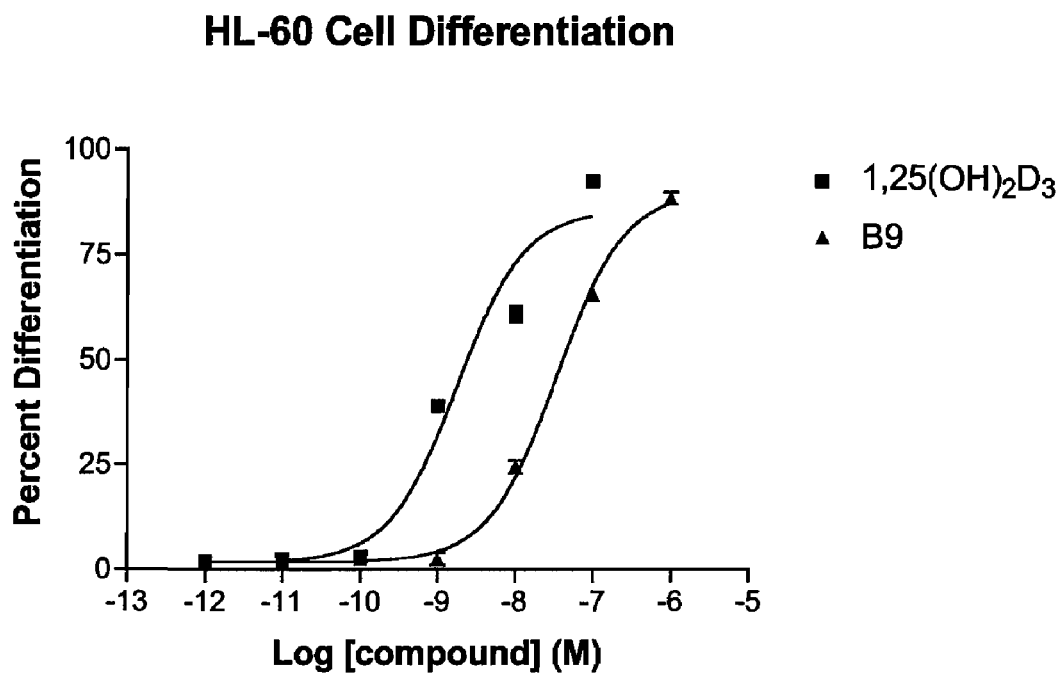

FIG. 2 illustrates that B-9 is about one log, i.e. ten times less potent than 1,25$(OH)_2D_3$ on HL-60 cell differentiation, i.e. causing the differentiation of HL-60 cells into monocytes. Although B-9 has lower in vitro cell differentiation activity than 1,25$(OH)_2D_3$, its activity on cell differentiation is still relatively significant. Thus, B-9 may be an excellent candidate for the treatment of psoriasis and cancer, especially against leukemia, colon cancer, breast cancer, skin cancer and prostate cancer. In addition, due to its relatively high cell differentiation activity, this compound provides a therapeutic agent for the treatment of various skin conditions including wrinkles, lack of adequate dermal hydration, i.e. dry skin, lack of adequate skin firmness, i.e. slack skin, and insufficient sebum secretion. Use of this compound thus not only results in moisturizing of skin but also improves the barrier function of skin.

Figure 3:
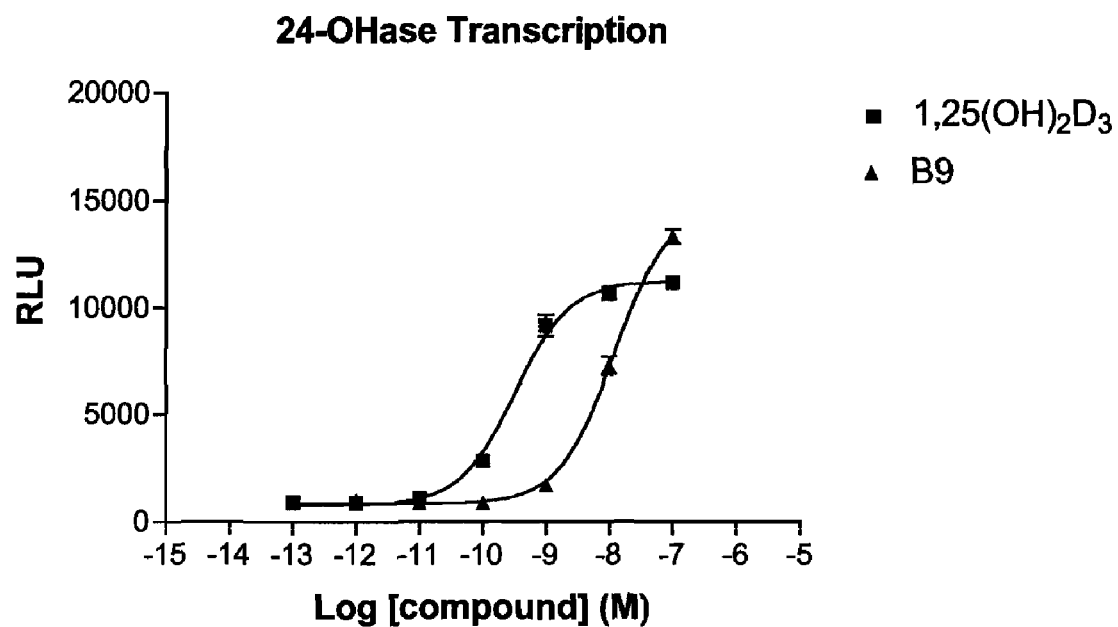

FIG. 3 illustrates that in bone cells the compound B-9 is about 30 times less potent than 1,25$(OH)_2D_3$ in increasing transcription of the 24-hydroxylase gene. Again, as with cell differentiation, although B-9's transcription activity is less than 1,25$(OH)_2D_3$, its activity in this regard is still relatively significant. This result, together with the cell differentiation activity of FIG. 2, suggests that B-9 will be very effective in psoriasis because it has direct cellular activity in causing cell differentiation, gene transcription, and in suppressing cell growth. These data also indicate that B-9 may have significant activity as an anti-cancer agent, especially against leukemia, colon cancer, breast cancer, skin cancer and prostate cancer.

The relatively strong activity of B-9 on HL-60 differentiation suggests it will be active in suppressing growth of parathyroid glands and in the suppression of the preproparathyroid gene.

Experimental Methods

Vitamin D Receptor Binding
Test Material
Protein Source

Full-length recombinant rat receptor was expressed in *E. coli* BL21 (DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in TEDK$_{50}$ (50 mM Tris, 1.5 mM EDTA, pH7.4, 5 mM DTT, 150 mM KCl) with 0.1% Chaps detergent. The receptor protein and ligand concentration were optimized such that no more than 20% of the added radiolabeled ligand was bound to the receptor.

Study Drugs

Unlabeled ligands were dissolved in ethanol and the concentrations determined using UV spectrophotometry (1,25 (OH)$_2$D$_3$: molar extinction coefficient=18,200 and $\lambda_{max}$=265 nm; Analogs: molar extinction coefficient=42,000 and $\lambda_{max}$=252 nm). Radiolabeled ligand ($^3$H-1,25(OH)$_2$D$_3$, ~159 Ci/mmole) was added in ethanol at a final concentration of 1 nM.

Assay Conditions

Radiolabeled and unlabeled ligands were added to 100 mcl of the diluted protein at a final ethanol concentration of ≦10%, mixed and incubated overnight on ice to reach binding equilibrium. The following day, 100 mcl of hydroxylapatite slurry (50%) was added to each tube and mixed at 10-minute intervals for 30 minutes. The hydroxylapaptite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand.

HL-60 Differentiation
Test Material
Study Drugs

The study drugs were dissolved in ethanol and the concentrations determined using UV spectrophotometry. Serial dilutions were prepared so that a range of drug concentrations could be tested without changing the final concentration of ethanol (≦0.2%) present in the cell cultures.

Cells

Human promyelocytic leukemia (HL60) cells were grown in RPMI-1640 medium containing 10% fetal bovine serum. The cells were incubated at 37° C. in the presence of 5% CO$_2$.

Assay Conditions

HL60 cells were plated at 1.2×10$^5$ cells/ml. Eighteen hours after plating, cells in duplicate were treated with drug. Four days later, the cells were harvested and a nitro blue tetrazolium reduction assay was performed (Collins et al., 1979; J. Exp. Med. 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

In vitro Transcription Assay

Transcription activity was measured in ROS 17/2.8 (bone) cells that were stably transfected with a 24-hydroxylase (24Ohase) gene promoter upstream of a luciferase reporter gene (Arbour et al., 1998). Cells were given a range of doses. Sixteen hours after dosing the cells were harvested and luciferase activities were measured using a luminometer.

RLU=relative luciferase units.

Intestinal Calcium Transport and Bone Calcium Mobilization

Male, weanling Sprague-Dawley rats were placed on Diet 11 (0.47% Ca) diet+AEK oil for one week followed by Diet 11 (0.02% Ca)+AEK oil for 3 weeks. The rats were then switched to a diet containing 0.47% Ca for one week followed by two weeks on a diet containing 0.02% Ca. Dose administration began during the last week on 0.02% calcium diet. Four consecutive ip doses were given approximately 24 hours apart. Twenty-four hours after the last dose, blood was collected from the severed neck and the concentration of serum calcium determined as a measure of bone calcium mobilization. The first 10 cm of the intestine was also collected for intestinal calcium transport analysis using the everted gut sac method.

Interpretation of Data

Summary of Biological Findings. This compound B-9 binds the VDR with slightly less affinity as the native hormone, and can be considered to be approximately one log, i.e. about 10 times, less potent than 1,25(OH)$_2$D$_3$ in this activity. B-9 also displays approximately 10 times less cell differentiation activity and about 30 times less in vitro gene transcription activity compared to 1,25(OH)$_2$D$_3$. However, this compound shows no activity in the bone and intestine at dose levels about 50 times higher or more than the dose levels of 1,25(OH)$_2$D$_3$ that show activity. Because this compound exhibits relatively significant cell differentiation and transcriptional activity, but no calcemic activity, it might be useful for treating patients with various autoimmune diseases, cancer, renal osteodystrophy, psoriasis or other skin diseases. B-9 might not only be useful in the treatment of the above listed diseases, but also in the prevention of the above listed diseases.

VDR binding, HL60 cell differentiation, and transcription activity. B-9 ($K_i$=1×10$^{-9}$M) is less active than the natural hormone 1α,25-dihydroxyvitamin D$_3$ ($K_i$=9×10$^{-11}$M) in its ability to compete with [$^3$H]-1,25(OH)$_2$D$_3$ for binding to the full-length recombinant rat vitamin D receptor (FIG. 1). B-9 displays about one log, i.e. 10 times less activity (EC$_{50}$=3× 10$^{-8}$M) in its ability (efficacy or potency) to promote HL-60 cell differentiation as compared to 1α,25-dihydroxyvitamin D$_3$ (EC$_{50}$=2×10$^{-9}$M) (See FIG. 2). Also, compound B-9 (EC$_{50}$=1×10$^{-8}$M) has about 30 times less transcriptional activity in bone cells than 1α,25-dihydroxyvitamin D$_3$ (EC$_{50}$=3×10$^{-10}$M) (See FIG. 3). These results suggest that B-9 will be very effective in psoriasis because it has direct cellular activity in causing cell differentiation, gene transcription, and in suppressing cell growth. These data also indicate that B-9 will have significant activity as an anti-cancer agent, especially against leukemia, colon cancer, breast cancer, skin cancer and prostate cancer, as well as against skin conditions such as dry skin (lack of dermal hydration), undue skin slackness (insufficient skin firmness), insufficient sebum secretion and wrinkles. It would also be expected to be very active in suppressing secondary hyperparathyroidism.

Calcium mobilization from bone and intestinal calcium absorption in vitamin D-deficient animals. Using vitamin D-deficient rats on a low calcium diet (0.02%), the activities of B-9 and 1,25(OH)$_2$D$_3$ in intestine and bone were tested. As expected, the native hormone (1,25(OH)$_2$D$_3$) increased serum calcium levels at all dosages (FIG. 4). The study reported in FIG. 4 shows that B-9 has relatively low, or little, activity in mobilizing calcium from bone. Even the administration of 35,100 pmol/day of B-9 for 4 consecutive days did not result in any mobilization of bone calcium whereas the native hormone 1,25(OH)$_2$D$_3$ had significant activity at 780 pmol/day where a substantial effect was seen.

Intestinal calcium transport was evaluated in the same group of animals using the everted gut sac method (FIG. 5). The study reported in FIG. 5 shows that B-9 has little or no intestinal calcium transport activity. Administration of 35,100 pmol/day of B-9 for 4 consecutive days did not result in any activity.

These results show that the compound B-9 does not promote intestinal calcium transport even when administered at 35,100 pmol/day. Thus, it may be concluded that B-9 has little, if any, intestinal calcium transport activity at the recommended lower doses to that of 1,25(OH)$_2$D$_3$.

These results illustrate that B-9 is an excellent candidate for numerous human therapies as described herein, and that it may be particularly useful in a number of circumstances such as suppression of secondary hyperparathyroidism of renal osteodystrophy, autoimmune diseases, cancer, numerous types of skin conditions, and psoriasis. B-9 is an excellent candidate for treating psoriasis because: (1) it has significant VDR binding, transcription activity and cellular differentiation activity; (2) it has little hypercalcemic liability, unlike 1,25(OH)$_2$D$_3$; and (3) it is easily synthesized. Since B-9 has significant binding activity to the vitamin D receptor, but has little ability to raise blood serum calcium, it may also be particularly useful for the treatment of secondary hyperparathyroidism of renal osteodystrophy.

These data also indicate that the compound B-9 of the invention may be especially suited for treatment and prophylaxis of human disorders which are characterized by an imbalance in the immune system, e.g. in autoimmune diseases, including multiple sclerosis, lupus, diabetes mellitus, host versus graft rejection, and rejection of organ transplants; and additionally for the treatment of inflammatory diseases, such as rheumatoid arthritis, asthma, and inflammatory bowel diseases such as celiac disease, ulcerative colitis and Crohn's disease. Acne, alopecia and hypertension are other conditions which may be treated with the compound B-9 of the invention.

The compounds of the invention of formula I, and particularly formula Ia, are also useful in preventing or treating obesity, inhibiting adipocyte differentiation, inhibiting SCD-1 gene transcription, and/or reducing body fat in animal subjects. Therefore, in some embodiments, a method of preventing or treating obesity, inhibiting adipocyte differentiation, inhibiting SCD-1 gene transcription, and/or reducing body fat in an animal subject includes administering to the animal subject, an effective amount of one or more of the compounds or a pharmaceutical composition that includes one or more of the compounds of formula I. Administration of the compound or the pharmaceutical compositions to the subject inhibits adipocyte differentiation, inhibits gene transcription, and/or reduces body fat in the animal subject. The animal may be a human, a domestic animal such as a dog or a cat, or an agricultural animal, especially those that provide meat for human consumption, such as fowl like chickens, turkeys, pheasant or quail, as well as bovine, ovine, caprine, or porcine animals.

For prevention and/or treatment purposes, the compounds of this invention defined by formula I, particularly B-9, may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds of formula I and particularly B-9, may be administered orally, topically, parenterally, rectally, nasally, sublingually or transdermally. The compound is advantageously administered by injection or by intravenous infusion or suitable sterile solutions, or in the form of liquid or solid doses via the alimentary canal, or in the form of creams, ointments, patches, or similar vehicles suitable for transdermal applications. A dose of from 0.01 µg to 1000 µg per day of the compounds I, particularly B-9, preferably from about 0.1 µg to about 500 µg per day, is appropriate for prevention and/or treatment purposes, such dose being adjusted according to the disease to be treated, its severity and the response of the subject as is well understood in the art. Since the compound exhibits specificity of action, each may be suitably administered alone, or together with graded doses of another active vitamin D compound—e.g. 1α-hydroxyvitamin D$_2$ or D$_3$, or 1α,25-dihydroxyvitamin D$_3$—in situations where different degrees of bone mineral mobilization and calcium transport stimulation is found to be advantageous.

Compositions for use in the above-mentioned treatments comprise an effective amount of the compounds I, particularly B-9, as defined by the above formula I and Ia as the active ingredient, and a suitable carrier. An effective amount of such compound for use in accordance with this invention is from about 0.01 µg to about 1000 µg per gm of composition, preferably from about 0.1 µg to about 500 µg per gram of composition, and may be administered topically, transdermally, orally, rectally, nasally, sublingually, or parenterally in dosages of from about 0.01 µg/day to about 1000 µg/day, and preferably from about 0.1 µg/day to about 500 µg/day.

The compounds I, particularly B-9, may be formulated as creams, lotions, ointments, topical patches, pills, capsules or tablets, suppositories, aerosols, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds I, particularly B-9, may be advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100µ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

We claim:

1. A compound having the formula:

I where $X_1$, $X_2$ and $X_3$, which may be the same or different, are each selected from hydrogen or a hydroxy-protecting group.
2. The compound of claim 1 wherein $X_3$ is hydrogen.
3. The compound of claim 1 wherein $X_1$ is hydrogen.
4. The compound of claim 1 wherein $X_1$, $X_2$ and $X_3$ are all t-butyldimethylsilyl.
5. A pharmaceutical composition containing an effective amount of at least one compound as claimed in claim 1 together with a pharmaceutically acceptable excipient.
6. The pharmaceutical composition of claim 5 wherein said effective amount comprises from about 0.01 µg to about 1000 µg per gram of composition.
7. The pharmaceutical composition of claim 5 wherein said effective amount comprises from about 0.1 µg to about 500 µg per gram of composition.
8. The compound (20R)-2α-methyl-19, 26, 19, 27-trinor-1α, 25-dihydroxyvitamin D3 having the formula:

Ia

9. A pharmaceutical composition containing an effective amount of (20R)-2α-methyl-19,26,27-trinor-1α,25-dihydroxyvitamin $D_3$ together with a pharmaceutically acceptable excipient.

10. The pharmaceutical composition of claim 9 wherein said effective amount comprises from about 0.01 µg to about 1000 µg per gram of composition.
11. The pharmaceutical composition of claim 9 wherein said effective amount comprises from about 0.1 µg to about 500 µg per gram of composition.
12. A method of treating psoriasis comprising administering to a subject with psoriasis an effective amount of a compound having the formula:

I where $X_1$, $X_2$ and $X_3$ which may be the same or different, are each selected from hydrogen or a hydroxy-protecting group.
13. The method of claim 12 wherein the compound is administered orally.
14. The method of claim 12 wherein the compound is administered parenterally.
15. The method of claim 12 wherein the compound is administered transdermally.
16. The method of claim 12 wherein the compound is administered topically.
17. The method of claim 12 wherein the compound is administered rectally.
18. The method of claim 12 wherein the compound is administered nasally.
19. The method of claim 12 wherein the compound is administered sublingually.
20. The method of claim 12 wherein the compound is administered in a dosage of from about 0.01 µg/day to about 1000 µg/day.
21. The method of claim 12 wherein the compound is (20R)-2α-methyl-19,26,27-trinor-1α,25-dihydroxyvitamin $D_3$ having the formula:

Ia

22. A method of treating a disease selected from the group consisting of leukemia, colon cancer, breast cancer, skin cancer or prostate cancer comprising administering to a subject with said disease an effective amount of a compound having the formula:

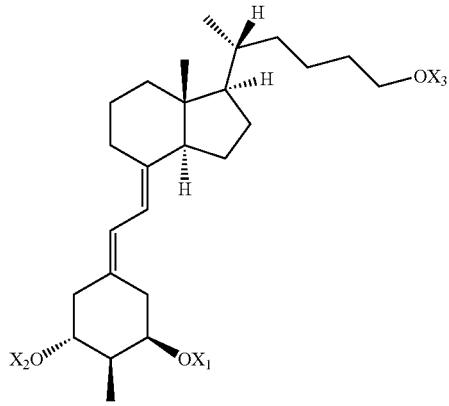

where $X_1$, $X_2$ and $X_3$ which may be the same or different, are each selected from hydrogen or a hydroxy-protecting group.

23. The method of claim 22 wherein the compound is administered orally.

24. The method of claim 22 wherein the compound is administered parenterally.

25. The method of claim 22 wherein the compound is administered transdermally.

26. The method of claim 22 wherein the compound is administered rectally.

27. The method of claim 22 wherein the compound is administered nasally.

28. The method of claim 22 wherein the compound is administered sublingually.

29. The method of claim 22 wherein the compound is administered in a dosage of from about 0.01 μg/day to about 1000 μg/day.

30. The method of claim 22 wherein the compound is (20R)-2α-methyl-19,26,27-trinor-1α,25-dihydroxyvitamin D$_3$ having the formula:

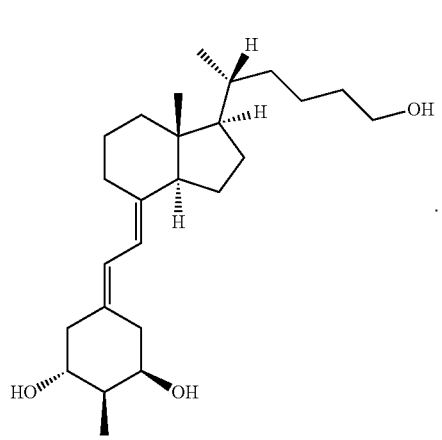

31. A method of treating an autoimmune disease selected from the group consisting of multiple sclerosis, lupus, diabetes mellitus, host versus graft rejection, and rejection of organ transplants, comprising administering to a subject with said disease an effective amount of a compound having the formula:

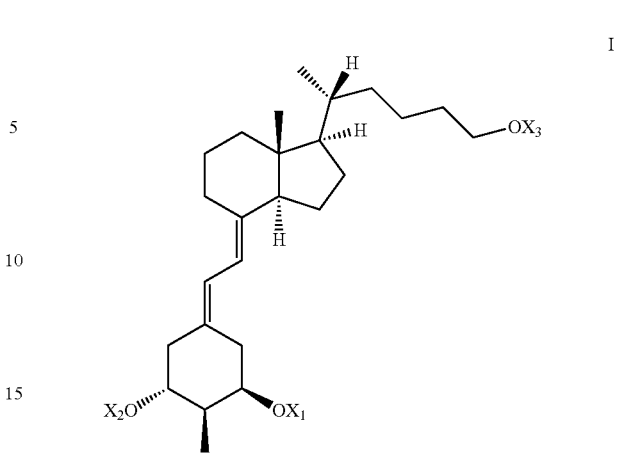

where $X_1$, $X_2$ and $X_3$ which may be the same or different, are each selected from hydrogen or a hydroxy-protecting group.

32. The method of claim 31 wherein the compound is administered orally.

33. The method of claim 31 wherein the compound is administered parenterally.

34. The method of claim 31 wherein the compound is administered transdermally.

35. The method of claim 31 wherein the compound is administered rectally.

36. The method of claim 31 wherein the compound is administered nasally.

37. The method of claim 31 wherein the compound is administered sublingually.

38. The method of claim 31 wherein the compound is administered in a dosage of from about 0.01 μg/day to about 1000 μg/day.

39. The method of claim 31 wherein the compound is (20R)-2α-methyl-19,26,27-trinor-1α,25-dihydroxyvitamin D$_3$ having the formula:

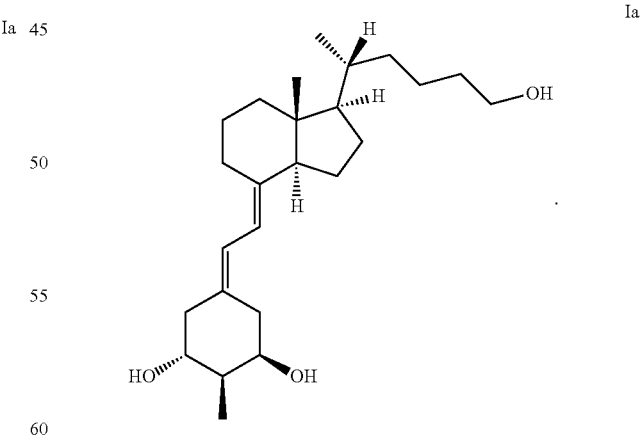

40. A method of treating an inflammatory disease selected from the group consisting of rheumatoid arthritis, asthma, and inflammatory bowel diseases, comprising administering to a subject with said disease an effective amount of a compound having the formula:

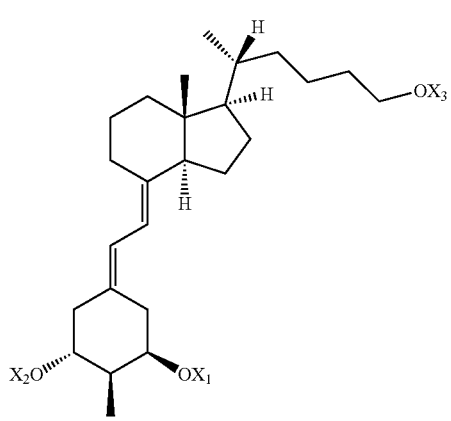

where $X_1$, $X_2$ and $X_3$, which may be the same or different, are each selected from hydrogen or a hydroxy-protecting group.

41. The method of claim 40 wherein the compound is administered orally.

42. The method of claim 40 wherein the compound is administered parenterally.

43. The method of claim 40 wherein the compound is administered transdermally.

44. The method of claim 40 wherein the compound is administered rectally.

45. The method of claim 40 wherein the compound is administered nasally.

46. The method of claim 40 wherein the compound is administered sublingually.

47. The method of claim 40 wherein the compound is administered in a dosage of from about 0.01 μg/day to about 1000 μg/day.

48. The method of claim 40 wherein the compound is (20R)-2α-methyl-19,26,27-trinor-1α,25-dihydroxyvitamin $D_3$ having the formula:

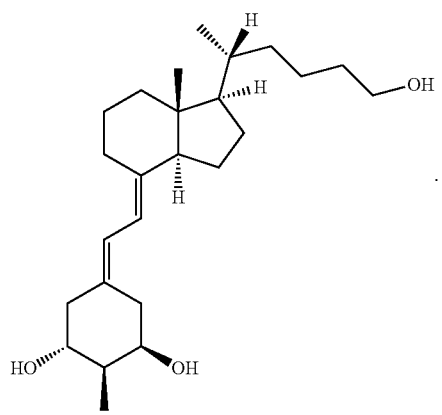

49. A method of treating a skin condition selected from the group consisting of wrinkles, lack of adequate skin firmness, lack of adequate dermal hydration and insufficient sebum secretion which comprises administering to a subject with said skin condition an effective amount of a compound having the formula:

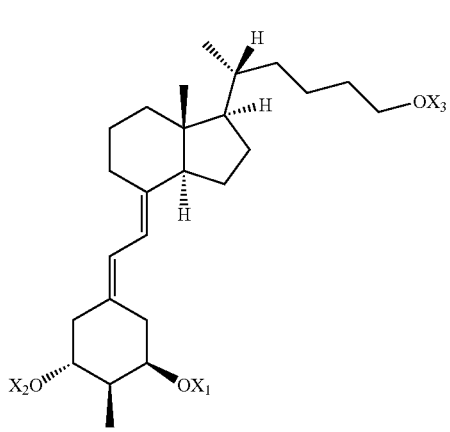

where $X_1$, $X_2$ and $X_3$ which may be the same or different, are each selected from hydrogen or a hydroxy-protecting group.

50. The method of claim 49 wherein the compound is administered orally.

51. The method of claim 49 wherein the compound is administered parenterally.

52. The method of claim 49 wherein the compound is administered transdermally.

53. The method of claim 49 wherein the compound is administered topically.

54. The method of claim 49 wherein the compound is administered rectally.

55. The method of claim 49 wherein the compound is administered nasally.

56. The method of claim 49 wherein the compound is administered sublingually.

57. The method of claim 49 wherein the compound is administered in a dosage of from about 0.01 μg/day to about 1000 μg/day.

58. The method of claim 49 wherein the compound is (20R)-2α-methyl-19,26,27-trinor-1α,25-dihydroxyvitamin $D_3$ having the formula:

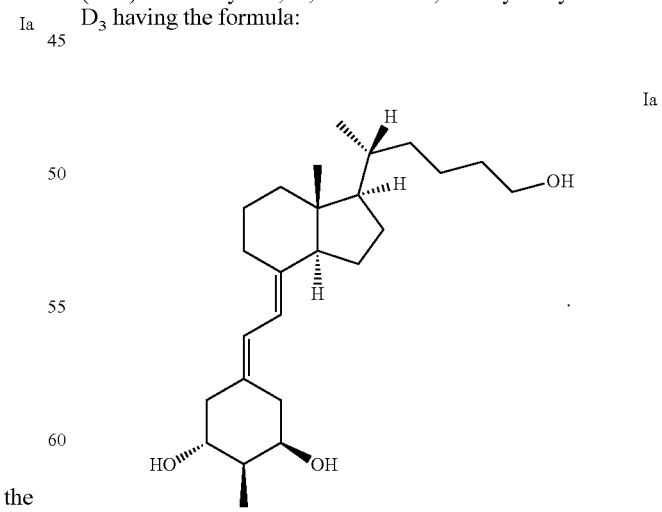

59. A method of treating renal osteodystrophy comprising administering to a subject with renal osteodystrophy an effective amount of a compound having the formula:

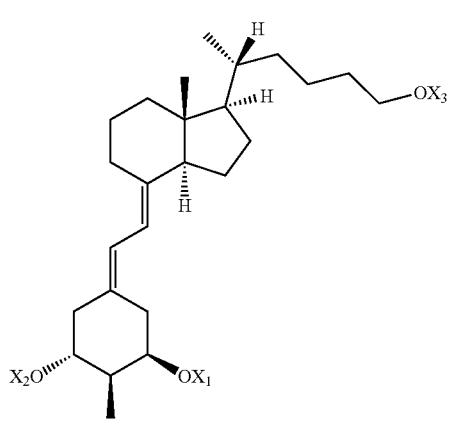

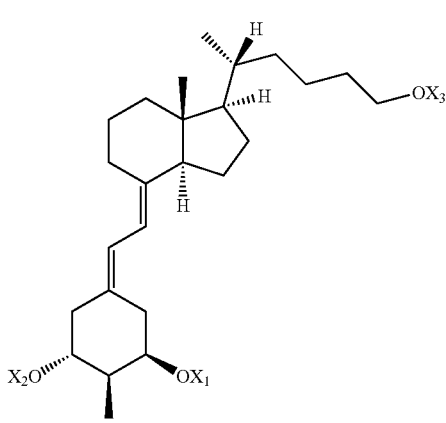

where $X_1$, $X_2$ and $X_3$, which may be the same or different, are each selected from hydrogen or a hydroxy-protecting group.

60. The method of claim 59 wherein the compound is administered orally.

61. The method of claim 59 wherein the compound is administered parenterally.

62. The method of claim 59 wherein the compound is administered transdermally.

63. The method of claim 59 wherein the compound is administered rectally.

64. The method of claim 59 wherein the compound is administered nasally.

65. The method of claim 59 wherein the compound is administered sublingually.

66. The method of claim 59 wherein the compound is administered in a dosage of from about 0.01 μg/day to about 1000 μg/day.

67. The method of claim 59 wherein the compound is (20R)-2α-methyl-19,26,27-trinor-1α,25-dihydroxyvitamin $D_3$ having the formula:

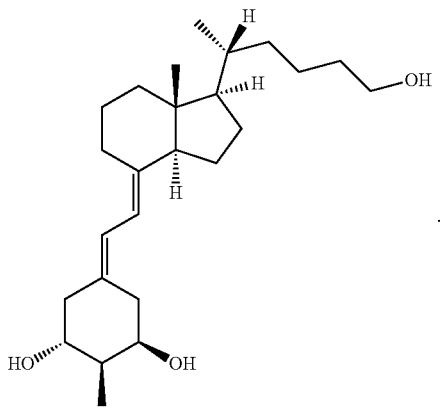

68. A method of treating obesity of an animal, inhibiting adipocyte differentiation, inhibiting SCD-1 gene transcription, and/or reducing body fat in an animal comprising administering to an animal in need thereof an effective amount of a compound having the formula:

where $X_1$, $X_2$ and $X_3$, which may be the same or different, are each selected from hydrogen or a hydroxy-protecting group.

69. The method of claim 68 wherein the compound is administered orally.

70. The method of claim 68 wherein the compound is administered parenterally.

71. The method of claim 68 wherein the compound is administered transdermally.

72. The method of claim 68 wherein the compound is administered rectally.

73. The method of claim 68 wherein the compound is administered nasally.

74. The method of claim 68 wherein the compound is administered sublingually.

75. The method of claim 68 wherein the compound is administered in a dosage of from about 0.01 μg/day to about 1000 μg/day.

76. The method of claim 68 wherein the compound is (20R)-2α-methyl-19,26,27-trinor-1α,25-dihydroxyvitamin $D_3$ having the formula:

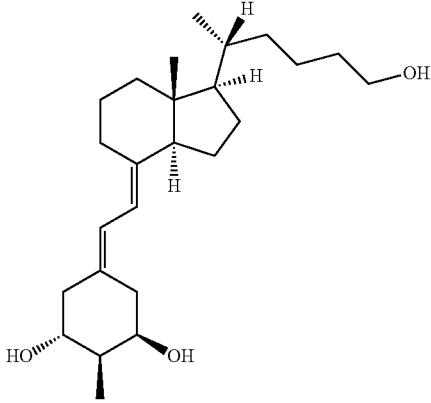

77. The method of claim 68 wherein the animal is a human.

78. The method of claim 68 wherein the animal is a domestic animal.

79. The method of claim 68 wherein the animal is an agricultural animal.

* * * * *